(12) United States Patent
Pollock et al.

(10) Patent No.: US 12,569,696 B2
(45) Date of Patent: Mar. 10, 2026

(54) WEARABLE MEDICAL SYSTEM (WMS) IMPLEMENTING WEARABLE CARDIOVERTER DEFIBRILLATOR (WCD) CAPTURING, RECORDING AND REPORTING AMBIENT SOUNDS

(71) Applicant: West Affum Holdings DAC, Dublin (IE)

(72) Inventors: Cameron G. Pollock, Kirkland, WA (US); Stacy Taylor, Kingston, WA (US); Kenneth F. Cowan, Everett, WA (US); Traci S. Umberger, Kirkland, WA (US); Gregory T. Kavounas, Bellevue, WA (US)

(73) Assignee: West Affum Holdings DAC, Dublin (IE)

( * ) Notice: Subject to any disclaimer, the term of this patent is extended or adjusted under 35 U.S.C. 154(b) by 525 days.

(21) Appl. No.: 18/073,659

(22) Filed: Dec. 2, 2022

(65) Prior Publication Data

US 2023/0277860 A1 Sep. 7, 2023

Related U.S. Application Data

(60) Provisional application No. 63/316,089, filed on Mar. 3, 2022.

(51) Int. Cl.
*A61N 1/39* (2006.01)

(52) U.S. Cl.
CPC ......... *A61N 1/3993* (2013.01); *A61N 1/3904* (2017.08)

(58) Field of Classification Search
CPC . A61N 1/3904; A61N 1/39046; A61N 1/3993
See application file for complete search history.

(56) References Cited

U.S. PATENT DOCUMENTS 3,724,455 A 4/1973 Unger
4,291,699 A 9/1981 Geddes et al.
(Continued)

FOREIGN PATENT DOCUMENTS

WO 9839061 A2 9/1998
WO 2016154425 A1 9/2016

OTHER PUBLICATIONS

Heartstart MRx and XL AED Algorithm—Application Note, Jul. 2001, Edition 2 Philips Healthcare, USA.
(Continued)

*Primary Examiner* — Eric D. Bertram
(74) *Attorney, Agent, or Firm* — Polsinelli PC

(57) ABSTRACT

A Wearable Medical System (WMS) that implements a wearable cardioverter defibrillator (WCD), includes a microphone and related improvements. The microphone can be on the same dongle as the cancel switch of the WCD. A user trigger module may permit the patient to perform a deliberate act and, in response, the system may start recording audio from the ambient sounds, including their own voice, and/or start recording the ECG. The deliberate act may even be a voice command by the patient that is parsed by a voice recognition module. The WMS may continuously record audio and then continuously discard it, and further stop the discarding if it detects a recording trigger. The WMS may create an exportable computer file that has audio-related data, which can have playable sound data or transcribed voice data.

15 Claims, 22 Drawing Sheets

PATIENT TRIGGERS
RECORDING OF ECG DATA

(56)                    References Cited

U.S. PATENT DOCUMENTS

| | | | |
|---|---|---|---|
| 4,583,524 A | 4/1986 | Hutchins | |
| 4,617,938 A | 10/1986 | Shimoni et al. | |
| 4,619,265 A | 10/1986 | Morgan et al. | |
| 4,895,151 A | 1/1990 | Grevis et al. | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bomn et al. | |
| 5,353,793 A | 10/1994 | Bomn | |
| RE34,800 E | 11/1994 | Hutchins | |
| 5,376,104 A | 12/1994 | Sakai et al. | |
| 5,381,803 A | 1/1995 | Herleikson et al. | |
| 5,394,892 A | 3/1995 | Kenny et al. | |
| 5,405,362 A | 4/1995 | Kramer et al. | |
| 5,425,749 A | 6/1995 | Adams | |
| 5,474,574 A | 12/1995 | Payne et al. | |
| 5,554,174 A | 9/1996 | Causey, III | |
| 5,601,612 A | 2/1997 | Gliner et al. | |
| 5,630,834 A | 5/1997 | Bardy | |
| 5,662,690 A | 9/1997 | Cole et al. | |
| 5,709,215 A | 1/1998 | Perttu et al. | |
| 5,769,872 A | 6/1998 | Lopin et al. | |
| 5,782,878 A | 7/1998 | Morgan et al. | |
| 5,792,204 A | 8/1998 | Snell | |
| 5,803,927 A | 9/1998 | Cameron et al. | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,068,651 A | 5/2000 | Brandell | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,351,671 B1 | 2/2002 | Myklebust et al. | |
| 6,356,785 B1 | 3/2002 | Snyder et al. | |
| 6,427,083 B1 | 7/2002 | Owen et al. | |
| 6,529,875 B1 | 3/2003 | Nakajima et al. | |
| 6,546,285 B1 | 4/2003 | Owen et al. | |
| 6,671,545 B2 | 12/2003 | Fincke | |
| 6,681,003 B2 | 1/2004 | Linder et al. | |
| 6,694,187 B1 | 2/2004 | Freeman | |
| 6,762,917 B1 | 7/2004 | Verbiest et al. | |
| 6,941,168 B2 | 9/2005 | Girouard | |
| 7,065,401 B2 | 6/2006 | Worden | |
| 7,149,576 B1 | 12/2006 | Baura et al. | |
| 7,336,994 B2 | 2/2008 | Hettrick et al. | |
| 7,379,771 B2 | 5/2008 | Kovac et al. | |
| 7,559,902 B2 | 7/2009 | Ting et al. | |
| 7,865,238 B2 | 1/2011 | Brink | |
| 7,870,761 B2 | 1/2011 | Valentine et al. | |
| 7,894,894 B2 | 2/2011 | Stadler et al. | |
| 7,974,689 B2 | 7/2011 | Volpe et al. | |
| 8,024,037 B2 | 9/2011 | Kumar | |
| 8,036,746 B2 | 10/2011 | Sanders | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,825,154 B2 | 9/2014 | Jorgenson et al. | |
| 8,838,235 B2 | 9/2014 | Cowan et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 8,996,101 B2 | 3/2015 | Zhang et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,533,165 B1 | 1/2017 | Gunderson | |
| 9,592,403 B2 | 3/2017 | Sullivan | |
| 9,757,579 B2 | 9/2017 | Foshee, Jr. et al. | |
| 9,757,581 B2 | 9/2017 | Sullivan et al. | |
| 10,016,614 B2 | 7/2018 | Sullivan | |
| 10,322,291 B2 | 6/2019 | Medema et al. | |
| 11,077,310 B1 | 8/2021 | Sullivan | |
| 11,103,717 B2 | 8/2021 | Sullivan et al. | |
| 11,160,990 B1 | 11/2021 | Sullivan et al. | |
| 11,363,958 B2 | 6/2022 | Nguyen et al. | |
| 2003/0158593 A1 | 8/2003 | Heilman et al. | |
| 2003/0187479 A1 | 10/2003 | Thong | |
| 2004/0049117 A1 | 3/2004 | Ideker et al. | |
| 2004/0220623 A1 | 11/2004 | Hess | |
| 2004/0230105 A1 | 11/2004 | Geva et al. | |
| 2005/0107833 A1 | 5/2005 | Freeman et al. | |
| 2005/0107834 A1 | 5/2005 | Freeman et al. | |
| 2005/0131476 A1 | 6/2005 | Kim et al. | |
| 2006/0017575 A1 | 1/2006 | McAdams | |
| 2006/0173364 A1 | 8/2006 | Clancy et al. | |
| 2007/0179539 A1 | 8/2007 | DeGroot et al. | |
| 2008/0033495 A1 | 2/2008 | Kumar | |
| 2008/0208070 A1 | 8/2008 | Snyder et al. | |
| 2008/0215103 A1 | 9/2008 | Powers et al. | |
| 2008/0306560 A1 | 12/2008 | Macho et al. | |
| 2008/0312708 A1 | 12/2008 | Snyder | |
| 2008/0312709 A1 | 12/2008 | Volpe et al. | |
| 2009/0005827 A1 | 1/2009 | Weintraub et al. | |
| 2009/0018595 A1 | 1/2009 | Bharmi et al. | |
| 2009/0171168 A1* | 7/2009 | Leyde | A61B 5/4094 |
| | | | 600/301 |
| 2010/0007413 A1 | 1/2010 | Herleikson et al. | |
| 2010/0114248 A1 | 5/2010 | Donofrio et al. | |
| 2010/0298899 A1 | 11/2010 | Donnelly et al. | |
| 2010/0331904 A1 | 12/2010 | Warren et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0022355 A1 | 1/2012 | Byrd et al. | |
| 2012/0059270 A1 | 3/2012 | Grunwald | |
| 2012/0108911 A1 | 5/2012 | Drysdale et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0277638 A1 | 11/2012 | Skelton et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0025132 A1 | 1/2014 | Libbus et al. | |
| 2014/0070957 A1 | 3/2014 | Longinotti-Buitoni et al. | |
| 2014/0150781 A1 | 6/2014 | Capua et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0037636 A1 | 2/2015 | Amsler et al. | |
| 2015/0039053 A1 | 2/2015 | Kaib et al. | |
| 2015/0105835 A1 | 4/2015 | Thakur et al. | |
| 2015/0265845 A1 | 9/2015 | Sullivan et al. | |
| 2015/0297107 A1 | 10/2015 | Sullivan et al. | |
| 2015/0297904 A1* | 10/2015 | Kavounas | A61B 5/25 |
| | | | 607/6 |
| 2015/0328472 A1 | 11/2015 | Sullivan et al. | |
| 2016/0000349 A1 | 1/2016 | Sullivan et al. | |
| 2016/0004831 A1 | 1/2016 | Carlson et al. | |
| 2016/0007877 A1 | 1/2016 | Felix et al. | |

(56) References Cited

U.S. PATENT DOCUMENTS

| | | | |
|---|---|---|---|
| 2016/0015329 A1 | 1/2016 | Kohlrausch et al. | |
| 2016/0067514 A1 | 3/2016 | Sullivan | |
| 2016/0074667 A1 | 3/2016 | Sullivan et al. | |
| 2016/0082277 A1 | 3/2016 | Foshee, Jr. et al. | |
| 2016/0121100 A1 | 5/2016 | Crone et al. | |
| 2016/0235320 A1 | 8/2016 | Sarkar et al. | |
| 2016/0278698 A1 | 9/2016 | Freeman et al. | |
| 2016/0331984 A1 | 11/2016 | Firoozabadi et al. | |
| 2017/0056682 A1 | 3/2017 | Kumar et al. | |
| 2017/0157416 A1 | 6/2017 | Medema et al. | |
| 2017/0182330 A1* | 6/2017 | Schneider | G16Z 99/00 |
| 2017/0252571 A1 | 9/2017 | Dascoli et al. | |
| 2018/0028083 A1 | 2/2018 | Greenhut et al. | |
| 2018/0093102 A1 | 4/2018 | Sullivan et al. | |
| 2018/0116537 A1 | 5/2018 | Sullivan et al. | |
| 2018/0117299 A1 | 5/2018 | Gustavson et al. | |
| 2018/0184933 A1 | 7/2018 | Sullivan et al. | |
| 2018/0185662 A1 | 7/2018 | Foshee, Jr. et al. | |
| 2018/0221648 A1 | 8/2018 | Gustavson et al. | |
| 2018/0318593 A1 | 11/2018 | Sullivan | |
| 2019/0030351 A1 | 1/2019 | Sullivan et al. | |
| 2019/0030352 A1 | 1/2019 | Sullivan et al. | |
| 2020/0164217 A1 | 5/2020 | Sullivan | |
| 2023/0019463 A1* | 1/2023 | Duke | G16H 15/00 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Translhoracic Defibrillation," JACC Journals, Dec. 1998, vol. 32 Issue 7, p. 2065-2071.

The LifeVest Network/Patient Data Management System, Zoll, 2015, 2000503 Rev A.

* cited by examiner

*SAMPLE COMPONENTS OF
A WEARABLE MEDICAL SYSTEM (WMS)
THAT IMPLEMENTS A WEARABLE
CARDIOVERTER DEFIBRILLATOR (WCD)*

*SAMPLE GARMENT*
*- INSIDE VIEW*

*SAMPLE GARMENT*
*- OUTSIDE VIEW*

*GARMENT AS WORN*
*– FRONT VIEW*

*GARMENT AS WORN*
*– BACK VIEW*

*SAMPLE GARMENT AS WORN*
*(ALTERNATE STYLE)*

408 THERAPY ELECTRODE PADS (BACK)

441 CABLE

443 DONGLE

444 ALERT BUTTON

404 THERAPY ELECTRODE PAD (FRONT)

405

407  409

499

446 HUB

447

406 HUB PLUG

416

400 UNIT

440 BATTERY (REMOVABLE)

483 MONITOR SCREEN

482 MONITOR LIGHT

401 HOUSING

484 SPEAKER

442

419 HUB PLUG RECEPTACLE

SAMPLE COMPONENTS ON GARMENT

SAMPLE COMPONENTS OF WMS UNIT
THAT IMPLEMENTS WCD AND/OR PACER

641 CABLE

643 DONGLE

676 MICROPHONE

644 CANCEL SWITCH OF WCD

630 PROCESSOR

600 UNIT

MICROPHONE HOSTED ON SAME DONGLE AS THE CANCEL SWITCH

741 CABLE

743
DONGLE

775
MICROPHONE OPENINGS

785
SPEAKER OPENINGS

789
VIBRATION MECHANISM

744
ALERT
BUTTON

730
PROCESSOR

700
UNIT

*MICROPHONE HOSTED ON THE SAME DONGLE AS THE ALERT BUTTON*

_PATIENT TRIGGERS_
_RECORDING OF AUDIO DATA_

900

METHODS FOR
STARTING AUDIO
RECORDING

1000

1061A                    1062A

1065
AMBIENT
SOUNDS 1071                    1072

1070
DELIBERATE
RECORDING
TRIGGER
INPUTS

1090
SOUND
RECORDINGS 1091                    1092

1008
TIME 1040    1042  1043        1045  1046

PATIENT TRIGGERS
RECORDING OF ECG DATA

Figure 12:
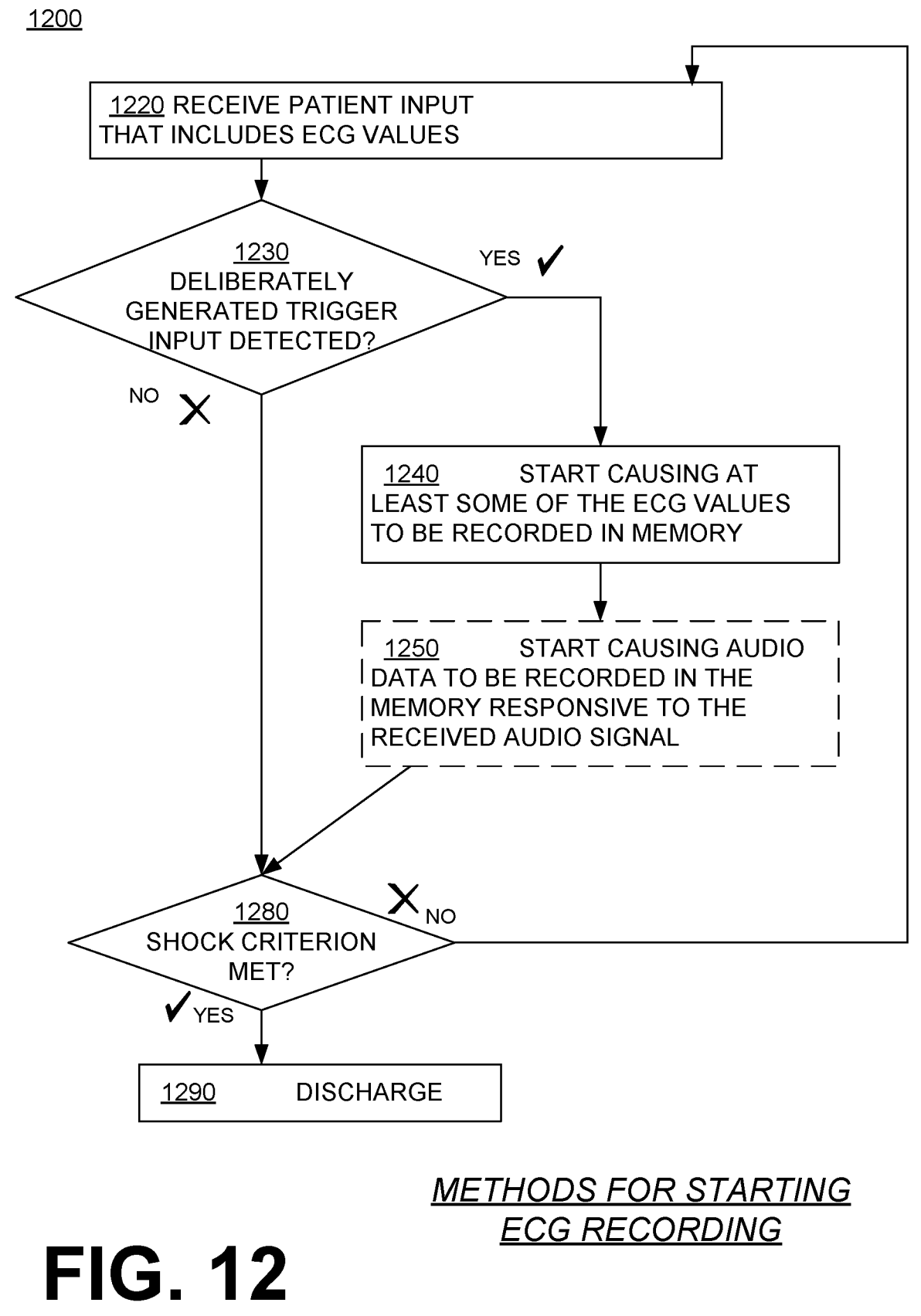

1200

1220 RECEIVE PATIENT INPUT THAT INCLUDES ECG VALUES

1230 DELIBERATELY GENERATED TRIGGER INPUT DETECTED?

YES ✔

NO ✗

1240       START CAUSING AT LEAST SOME OF THE ECG VALUES TO BE RECORDED IN MEMORY

1250       START CAUSING AUDIO DATA TO BE RECORDED IN THE MEMORY RESPONSIVE TO THE RECEIVED AUDIO SIGNAL

1280 SHOCK CRITERION MET?

✗ NO

✔ YES

1290       DISCHARGE

*METHODS FOR STARTING ECG RECORDING*

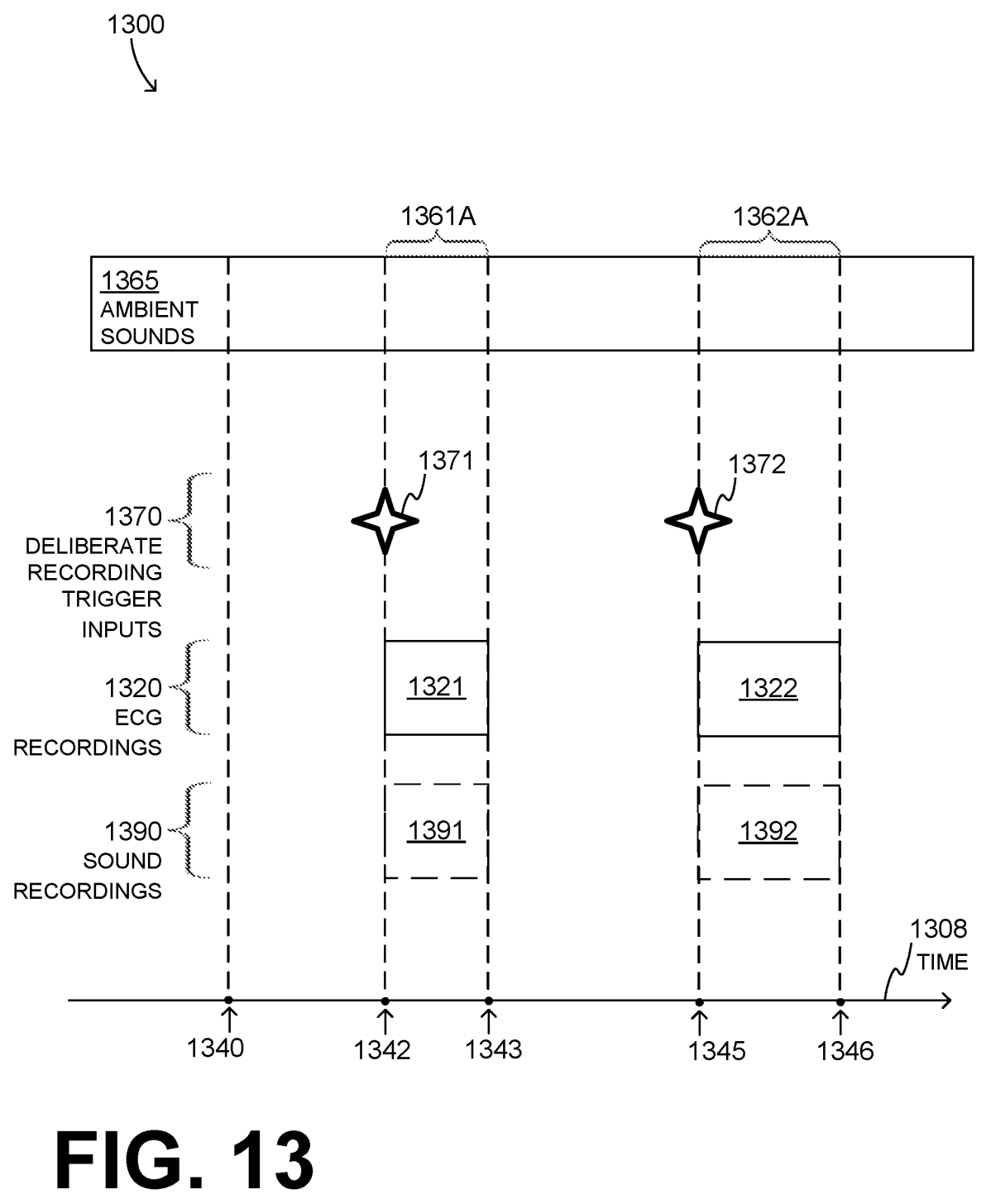

1365
AMBIENT
SOUNDS 1371                        1372

1370
DELIBERATE
RECORDING
TRIGGER
INPUTS

1320
ECG
RECORDINGS 1321                        1322

1390
SOUND
RECORDINGS 1391                        1392

1308
TIME 1340        1342    1343              1345    1346

FIG. 13

USER TRIGGER MODULE
IMPLEMENTED BY VOICE
RECOGNITION MODULE

1545
USER
TRIGGER
MODULE

1544
CANCEL
SWITCH

USER TRIGGER MODULE
IMPLEMENTED BY THE
CANCEL SWITCH

1645
USER
TRIGGER
MODULE

1680 TOUCHSCREEN

PRESS HERE
TO START
RECORDING

SAY WHAT
YOU ARE
EXPERIENCING

1681 MESSAGE

1671

1640
PERIPHERAL DEVICE

1600
UNIT

1676 MICROPHONE

USER TRIGGER MODULE
IMPLEMENTED IN
PERIPHERAL DEVICE

KEEPING RECORDED AUDIO DATA
RESPONSIVE TO RECORDING TRIGGER

_EVOLUTION OF MEMORY_
_STORING AUDIO DATA_

FIG. 20    METHODS FOR WMS

<u>COMPUTER FILE IS A SOUND FILE</u>

_AUDIO DATA AS VOICE TRANSCRIPTION IN PATIENT RECORD, SEEN VIA USER INTERFACE (UI)_

2300

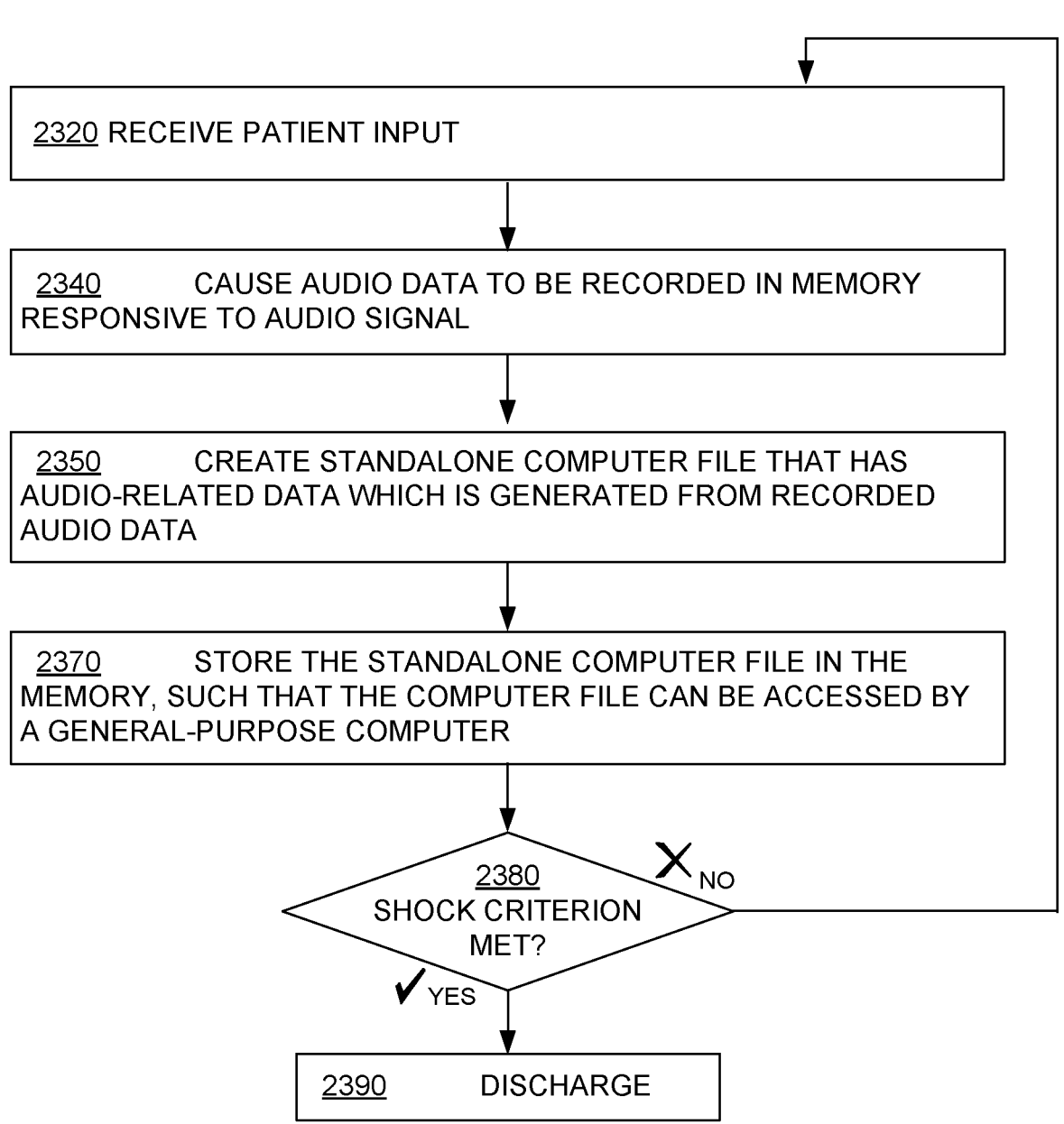

2320 RECEIVE PATIENT INPUT

2340    CAUSE AUDIO DATA TO BE RECORDED IN MEMORY RESPONSIVE TO AUDIO SIGNAL

2350    CREATE STANDALONE COMPUTER FILE THAT HAS AUDIO-RELATED DATA WHICH IS GENERATED FROM RECORDED AUDIO DATA

2370    STORE THE STANDALONE COMPUTER FILE IN THE MEMORY, SUCH THAT THE COMPUTER FILE CAN BE ACCESSED BY A GENERAL-PURPOSE COMPUTER

2380
SHOCK CRITERION MET?

X NO

✓ YES

2390    DISCHARGE

FIG. 23

_METHODS FOR WMS_

WEARABLE MEDICAL SYSTEM (WMS) IMPLEMENTING WEARABLE CARDIOVERTER DEFIBRILLATOR (WCD) CAPTURING, RECORDING AND REPORTING AMBIENT SOUNDS

CROSS REFERENCE TO RELATED APPLICATIONS

The present application claims the benefit of U.S. Application No. 63/316,089 filed on Mar. 3, 2022 which is incorporated herein by reference in its entirety.

BACKGROUND

A wearable medical system (WMS) is an advanced form of a medical system. A WMS typically includes one or more wearable components that a patient can wear or carry, and possibly other components that can be portable, or stationary such as base station and/or an electric charger. The WMS may also include one or more associated software packages, such as software applications (apps), which can be hosted by the wearable component, and/or by a mobile device, and/or by a remote computer system that is accessible via a communications network such as the internet, and so on.

A WMS typically includes a sensor that can sense when a parameter of the patient is problematic, and cause the WMS to initiate an appropriate action. The appropriate action could be for the WMS to communicate with the patient or even with a bystander, to transmit an alert to a remotely located clinician, and to even administer treatment or therapy to the patient by itself. A WMS may actually include more than one sensor, which may sense more than one parameter of the patient. The multiple parameters may be used for determining whether or not to administer the treatment or therapy, or be suitable for detecting different problems and/or for administering respectively different treatments or therapies to the patient.

A WMS may also include the appropriate components for implementing a wearable cardioverter defibrillator (WCD), a pacer, and so on. Such a WMS can be for patients who have an increased risk of sudden cardiac arrest (SCA). In particular, when people suffer from some types of heart arrhythmias, the result may be that blood flow to various parts of the body is reduced. Some arrhythmias may result in SCA, which can lead to death very quickly, unless treated within a short time, such as 10 minutes. Some observers may have thought that SCA is the same as a heart attack, but it is not. For such patients, an external cardiac defibrillator can deliver a shock through the heart, and restore its normal rhythm. The problem is that it is hard for an external cardiac defibrillator to be brought to the patient within that short time. One solution, therefore, is for such patients to be given a WMS that implements a WCD. This solution is at least temporary and, after a while such as two months, the patient may instead receive a surgically implantable cardioverter defibrillator (ICD), which would then become a permanent solution.

A WMS that implements a WCD typically includes a harness, vest, belt, or other garment that the patient is to wear. The WMS system further includes additional components that are coupled to the harness, vest, or other garment. Alternately, these additional components may be adhered to the patient's skin by adhesive. These additional components include a unit that has a defibrillator, and sensing and therapy electrodes. When the patient wears this WMS, the sensing electrodes may make good electrical contact with the patient's skin and therefore can help sense the patient's Electrocardiogram (ECG). If the unit detects a shockable heart arrhythmia from the ECG, then the unit delivers an appropriate electric shock to the patient's body through the therapy electrodes. The shock can pass through the patient's heart and may restore its normal rhythm, thus saving their life. Some WMSs even record and store the ECG of the patient, and make it available for further review by clinicians.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventors. This approach in and of itself may also be inventive.

BRIEF SUMMARY

The present description gives instances of Wearable Medical Systems (WMSs), storage media that may store programs, and methods, the use of which may help overcome problems and limitations of the prior art.

A Wearable Medical System (WMS) that implements a wearable cardioverter defibrillator (WCD), includes a microphone and related improvements. The microphone can be on the same dongle as the cancel switch of the WCD. A user trigger module may permit the patient to perform a deliberate act and, in response, the system may start recording audio from the ambient sounds, including their own voice, and/or start recording the ECG. The deliberate act may even be a voice command by the patient that is parsed by a voice recognition module. The WMS may continuously record audio and then continuously discard it, and further stop the discarding if it detects a recording trigger. The WMS may create an exportable computer file that has audio-related data, which can have playable sound data or transcribed voice data.

An advantage and/or benefit of the microphone's placement on the dongle arises when the patient wears the dongle on their chest. That places the microphone closer to the patient's mouth than, say, where the main electronics are, and therefore the microphone can capture better the patient's voice, and help make it more distinguishable over ambient sounds in a recording or live situation. This will further help with any transcription made in the future—it will be more accurate.

An advantage and/or benefit of enabling the patient to trigger recording of their ECG, and/or of ambient sounds, is that the eventual patient record will also have audio data that is useful for review by a clinician. The stored audio can be accessed by EMTs after arriving at the scene, or even later by the patient's physician or suitable personnel. For example, the EMT can access the audio to help determine what happened to the patient to better determine the appropriate treatment. Another advantage and/or benefit is that the system may end up recording events that might not be sensed otherwise. This includes events when the patient is experiencing symptoms of a medical event, such as chest pain, elevated heart rate, dizziness, shortness of breath, etc. This audio data may be in the form of computer files, perhaps one for each episode. This advantage and/or benefit can be enhanced in embodiments where the computer file includes the ECG at the time, in other words, when the audio data is added to the episode file.

An advantage and/or benefit of continuously recording audio, continuously discarding it, but then stopping the discarding is that audio recordings can be kept that were recorded even before the recording trigger was detected. If the recording trigger to start the recording was a voice command by the patient to "start" the recording, then the resulting audio recording that is actually preserved may even include that voice command.

An advantage and/or benefit of creating an exportable computer file that also includes audio-related data is that a clinician who reviews the patient record will have a better sense of what was happening, and better understand the patient's experience. This advantage and/or benefit can be enhanced in embodiments where the patient has directly recorded messages by speaking after knowing that the recording has started, and thus in effect has left messages for the clinician about the patient's experience.

As such, it will be appreciated that results of embodiments are larger than the sum of their individual parts, and have utility.

These and other features and advantages of the claimed invention will become more readily apparent in view of the embodiments described and illustrated in this specification, namely in this written specification and the associated drawings.

BRIEF DESCRIPTION OF THE DRAWINGS

FIG. 12 is a flowchart for illustrating sample methods according to embodiments.

FIG. 13 is a timing diagram showing sample durations of ECG data recordings and optionally also of concurrent audio data recordings resulting from deliberate recording triggers by the patient, according to embodiments.

FIG. 11 is implemented by a voice recognition module.

FIG. 11 is implemented by the cancel switch of the WMS system.

FIG. 11 is implemented in a peripheral device of the WMS system.

FIG. 23 is a flowchart for illustrating sample methods according to embodiments.

DETAILED DESCRIPTION

As has been mentioned, the present description is about wearable medical systems (WMS) that implement wearable cardioverter defibrillators (WCD). Embodiments are now described in more detail.

A wearable medical system (WMS) that implements a wearable cardioverter defibrillator (WCD) according to embodiments may protect an ambulatory patient by electrically restarting their heart if needed. Such a WMS may have a number of components. These components can be provided separately as modules that can be interconnected, or can be combined with other components, and so on. Examples are now described.

Figure 1:
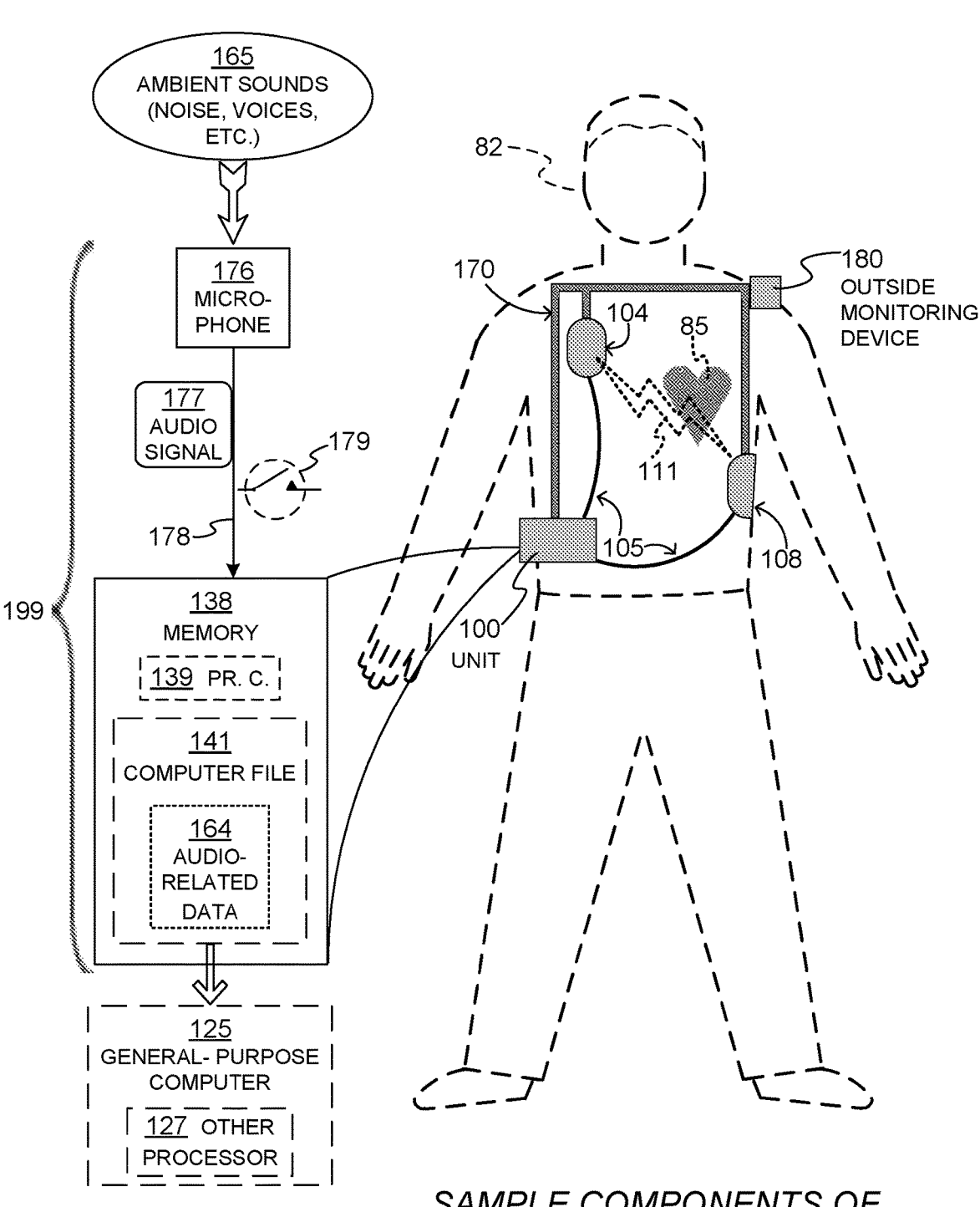
FIG. 1 is a diagram of sample components of a wearable medical system (WMS) that implements a wearable cardioverter defibrillator (WCD), and which is made according to embodiments.

FIG. 1 depicts a patient 82. The patient 82 may also be referred to as the person 82 and/or wearer 82, since the patient 82 is wearing and/or carrying components of a WMS. These components are indicated as 199.

The patient 82 is ambulatory, which means that, while wearing the wearable component(s) of the WMS, the patient 82 can walk around, be in a vehicle, and so on. In other words, the patient 82 is not necessarily bed-ridden. While the patient 82 may be considered to be also a "user" of the WMS, this definition is not exclusive to the patient 82. For instance, a user of the WMS may also be a clinician such as a doctor, nurse, emergency medical technician (EMT), or other similarly tasked and/or empowered individual or group of individuals. In some cases, a user may even be a bystander. The particular context of these and other related terms within this description should be interpreted accordingly.

A WMS that implements a WCD according to embodiments can be configured to defibrillate the patient who is wearing the designated components of the WMS. Defibrillating can be by the WMS delivering an electrical charge to the patient's body in the form of an electric shock. The electric shock can be delivered in one or more pulses.

In particular, FIG. 1 also depicts components of a WMS that implements a WCD and is made according to embodiments. One such component is a support structure 170 that is wearable by the ambulatory patient 82. Accordingly, the support structure 170 can be configured to be worn by the ambulatory patient 82 for at least several hours per day, and also during the night. That, for at least several days, and maybe even a few months. It will be understood that the support structure 170 is shown only generically in FIG. 1, and in fact partly conceptually. FIG. 1 is provided merely to illustrate concepts about the support structure 170, and is not to be construed as limiting how the support structure 170 is implemented, or how it is worn.

The support structure 170 can be implemented in many different ways. For example, it can be implemented in a single component or a combination of multiple components. In embodiments, the support structure 170 could include a vest, a half-vest, a garment, etc. In such embodiments such items can be worn similarly to analogous articles of clothing. In embodiments, the support structure 170 could include a harness, one or more belts or straps, etc. In such embodiments, such items can be worn by the patient around the torso, hips, over the shoulder, etc. In embodiments, the support structure 170 can include a container or housing, which can even be waterproof. In such embodiments, the support structure can be worn by being attached to the patient's body by adhesive material, for example as shown and described in U.S. Pat. No. 8,024,037. The support structure 170 can even be implemented as described for the support structure of US Pat. App. No. US2017/0056682, which is incorporated herein by reference. Of course, in such embodiments, the person skilled in the art will recognize that additional components of the WMS can be in the housing of a support structure instead of being attached externally to the support structure, for example as described in the US2017/0056682 document. There can be other examples.

The embodiments of FIG. 1 include a sample unit 100. In embodiments, the unit 100 is sometimes called a main electronics module. In embodiments, the unit 100 implements an external defibrillator. In embodiments, the unit 100 implements an external pacer instead of, or in addition to, an external defibrillator. In embodiments that include a pacer, the WMS may detect when the patient's heart rhythm slows down or when the patient has asystole, and the pacer may pace to increase the heart rate. In such embodiments, the WMS may pace the patient first, and hopefully not have to resort to the full intervention of defibrillation. Of course, if the patient does not respond to the pacing and their heart rhythm deteriorates further, the WMS may then later cause one or more defibrillation shocks to be delivered.

The embodiments of FIG. 1 also include sample therapy electrodes 104, 108, which are electrically coupled to unit 100 via electrode leads 105. The therapy electrodes 104, 108 are also called defibrillation electrodes or just electrodes. The therapy electrodes 104, 108 can be configured to be worn by the patient 82 in a number of ways. For instance, the unit 100 and the therapy electrodes 104, 108 can be coupled to the support structure 170, directly or indirectly. In other words, the support structure 170 can be configured to be worn by the ambulatory patient 82 so as to maintain at least one of the therapy electrodes 104, 108 on the body of the ambulatory patient 82, while the patient 82 is moving around, etc. The therapy electrodes 104, 108 can be thus maintained on the body by being attached to the skin of the patient 82, simply pressed against the skin directly or through garments, etc. In some embodiments the therapy electrodes 104, 108 are not necessarily pressed against the skin, but become biased that way upon sensing a condition that could merit intervention by the WMS. In addition, many of the components of the unit 100 can be considered coupled to the support structure 170 directly, or indirectly via at least one of the therapy electrodes 104, 108.

When the therapy electrodes 104, 108 make good electrical contact with the body of the patient 82, the unit 100 can administer, via the therapy electrodes 104, 108, a brief, strong electric pulse 111 through the body. The pulse 111 is also known as defibrillation pulse, shock, defibrillation shock, therapy, electrotherapy, therapy shock, etc. The pulse 111 is intended to go through and restart the heart 85, in an effort to save the life of the patient 82. The defibrillation pulse 111 can have an energy suitable for its purpose, such as at least 100 Joule (J), 200 J, 300 J, and so on. For pacer embodiments, the pulse 111 could alternately be depicting a pacing pulse. At least some of the stored electrical charge can be caused to be discharged via at least two of the therapy electrodes 104, 108 through the ambulatory patient 82, so as to deliver to the ambulatory patient 82 a pacing sequence of pacing pulses. The pacing pulses may be periodic, and thus define a pacing period and the pacing rate. There is no requirement, however, that the pacing pulses be exactly periodic. A pacing pulse can have an energy suitable for its purpose, such as at most 10 J, 5 J, usually about 2 J, and so on. The pacer therefore is delivering current to the heart to start a heartbeat. In either case, the pulse 111 has a waveform suitable for this purpose.

A prior art defibrillator typically decides whether to defibrillate or not based on an ECG signal of the patient. However, the unit 100 may initiate defibrillation, or hold-off defibrillation, based on a variety of inputs, with the ECG signal merely being one of these inputs.

A WMS that implements a WCD according to embodiments can collect data about one or more parameters of the patient 82. For collecting such data, the WMS may optionally include at least an outside monitoring device 180. The device 180 is called an "outside" device because it could be provided as a standalone device, for example not within the housing of the unit 100. The device 180 can be configured to sense or monitor at least one local parameter. A local parameter can be a parameter of the patient 82, or a parameter of the WMS, or a parameter of the environment, as described later in this document.

For some of these parameters, the device 180 may include one or more sensors or transducers. Each one of such sensors can be configured to sense a parameter of the patient 82, or of the environment, and to render an input responsive to the sensed parameter. In some embodiments the input is quantitative, such as values of a sensed parameter; in other embodiments the input is qualitative, such as informing whether or not a threshold is crossed, and so on. Such inputs about the patient 82 are also called physiological inputs and patient inputs. In embodiments, a sensor can be construed more broadly, as encompassing more than one individual sensors.

Optionally, the device 180 is physically coupled to the support structure 170. In addition, the device 180 may be communicatively coupled with other components that are coupled to the support structure 170, such as with the unit 100. Such communication can be implemented by the device 180 itself having a communication module, as will be deemed applicable by a person skilled in the art in view of this description.

A WMS that implements a WCD according to embodiments preferably includes sensing electrodes, which can sense an ECG of the patient. In embodiments, the device 180 stands for such sensing electrodes. In those embodiments, the sensed parameter of the patient 82 is the ECG of the patient, the rendered input can be time values of a waveform of the ECG signal, and so on.

In embodiments, one or more of the components of the shown WMS may be customized for the patient 82. This customization may include a number of aspects. For instance, the support structure 170 can be fitted to the body of the patient 82. For another instance, baseline physiological parameters of the patient 82 can be measured for various scenarios, such as when the patient is lying down (various orientations), sitting, standing, walking, running, and so on. These baseline physiological parameters can be the heart rate of the patient 82, motion detector outputs, one for each scenario, etc. The measured values of such baseline physiological parameters can be used to customize the WMS, in order to make its diagnoses more accurate, since patients' bodies differ from one another. Of course, such parameter values can be stored in a memory of the WMS, and so on. Moreover, a programming interface can be made according to embodiments, which receives such measured values of baseline physiological parameters. Such a programming interface may input automatically these in the WMS, along with other data.

The support structure 170 is configured to be worn by the ambulatory patient 82 so as to maintain the therapy electrodes 104, 108 on a body of the patient 82. As mentioned before, the support structure 170 can be advantageously implemented by clothing or one or more garments. Such clothing or garments do not have the function of covering a person's body as a regular clothing or garments do, but the terms "clothing" and "garment" are used in this art for certain components of the WMS intended to be worn on the human body in the same way as clothing and garments are. In fact, such clothing and garments of a WMS can be of different sizes for different patients, and even be custom-fitted around the human body. And, regular clothing can often be worn over portions or all of the support structure 170. Examples of the support structure 170 are now described.

Figure 2A:
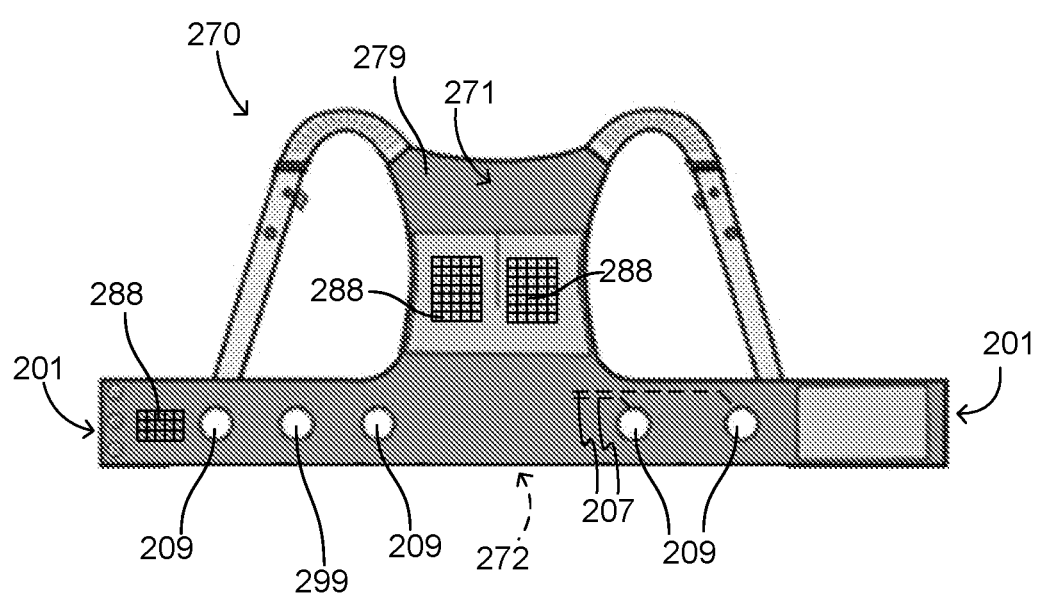
FIG. 2A is a diagram showing a view of the inside of a sample garment embodiment that can be a support structure of a WMS that implements a WCD, such as that of FIG. 1.

FIG. 2A shows a support structure 270 of a WMS that implements a WCD, such as the support structure 170 of FIG. 1. The support structure 270 is implemented by a vest-like wearable garment 279 that is shown flat, as if placed on a table. The inside side 271 of the garment 279 is seen as one looks at the diagram from the top, and it is the side contacting the body of the wearer when the garment 279 is worn. The outside side 272 of the garment 279 is opposite the inside side 271. To be worn, tips 201 can be brought together while surrounding the torso, and affixed to each other, either at their edges or partly overlapping. Appropriate mechanisms can hold together the tips 201, such as hooks and loops, Velcro® material, and so on.

The garment 279 can be made of suitable combinations of materials, such as fabric, linen, plastic, and so on. In places, the garment 279 can have two adjacent surfaces for defining between them pockets for the pads of the electrodes, for enclosing the leads or wires of the electrodes, and so on. Moreover, in FIG. 2A one can see meshes 288 which are the interior side of pockets accessible from the outside. The meshes can be made from flexible material such as loose netting, and so on.

ECG signals in a WMS that implements a WCD may sometimes include too much electrical noise for analyzing the ECG signal. To ameliorate the problem, multiple ECG sensing electrodes are provided in embodiments. These multiple ECG sensing electrodes define different vectors for sensing ECG signals along different ECG channels. These different ECG channels therefore present alternative options for analyzing the patient's ECG signal. The patient impedance along each ECG channel may also be sensed, and thus be part of the patient input.

In the example of FIG. 2A, multiple ECG sensing electrodes 209 are provided, which can be seen protruding from the inside surface of the garment 279. These ECG sensing electrodes 209 can be affixed to the inside surface of the garment 279, while their leads or wires 207 can be located mostly or completely within the garment 279. These ECG sensing electrodes 209 are intended to contact the skin of the person when the garment 279 is worn, and can be made from suitable material for good electrical contact. Such a material can be a metal, such as silver. An additional ECG-sensing electrode 299 may play the role of a Right Leg Drive (RLD) in the ECG analysis. It will be understood that "RLD" is a name for a specific ECG lead, and embodiments do not require that the electrode 299 be actually placed on the patient's right leg.

Figure 2B:
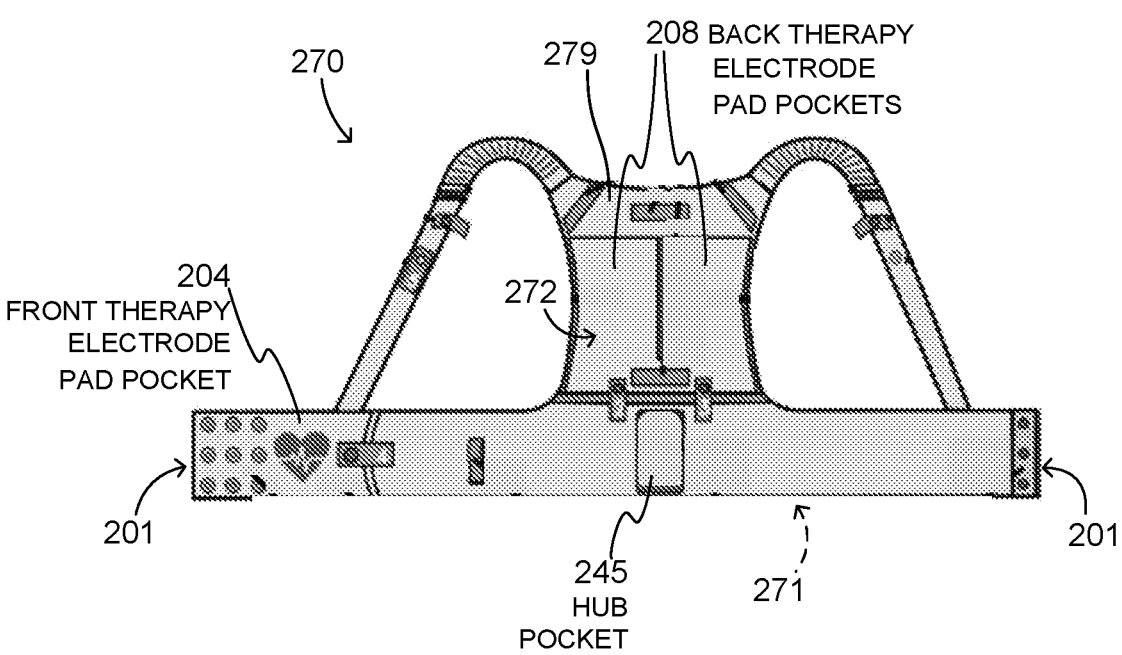
FIG. 2B is a diagram showing a view of the outside of the sample garment of FIG. 2A.

FIG. 2B shows the outside side 272 of the garment 279. One can appreciate that pockets are included that are accessible from the outside, such as a hub pocket 245. In addition a pocket 204 is provided for a front therapy electrode pad, plus two pockets 208 are provided for two back therapy electrode pads. The pads of the therapy electrodes can be placed in the pockets 204, 208, and contact the skin of the patient through the respective meshes 288 that were seen in FIG. 2A. The electrical contact can be facilitated by conductive fluid that can be deployed in the area, when the time comes for a shock.

Figure 2C:
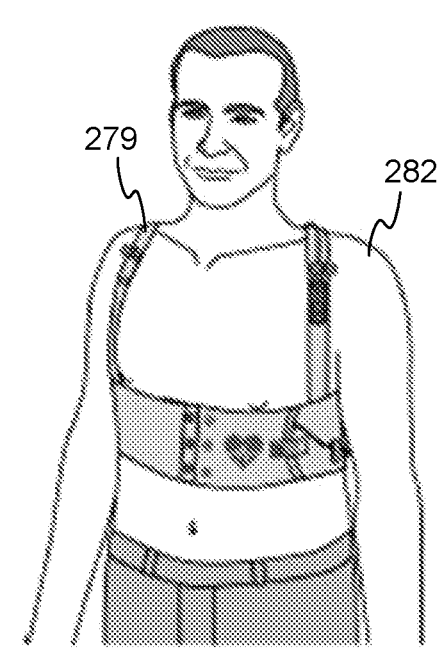
FIG. 2C is a diagram showing a front view of how the sample garment of FIGS. 2A and 2B is intended to be worn by a patient.

FIG. 2C is a diagram showing a front view of how the garment 279 would be worn by a patient 282. It will be appreciated that the previously described ECG sensing electrodes 209, 299 of FIG. 2A are maintained against the body of the patient 282 from the inside side of the garment 279, and thus are not visible in FIG. 2C.

Figure 2D:
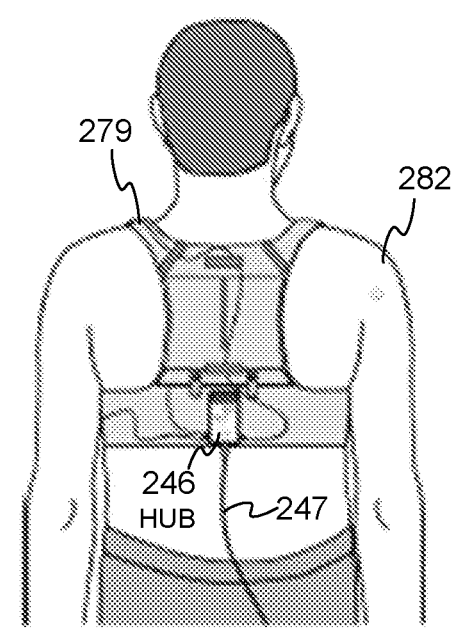
FIG. 2D is a diagram showing a back view of how the sample garment of FIGS. 2A and 2B is intended to be worn by a patient.

FIG. 2D is a diagram showing the back view of FIG. 2C. A hub 246 has been placed in the hub pocket 245 that is shown in FIG. 2B. A cable 247 emerges from the hub 246, which can be coupled with a unit for the system, as described later in this document.

FIGS. 2A-2D do not show any physical support for a unit such as the unit 100 of FIG. 1. In these embodiments, such a unit may be carried in a purse, on a belt, by a strap over the shoulder, or additionally by further adapting the garment 279, and so on.

Figure 3:
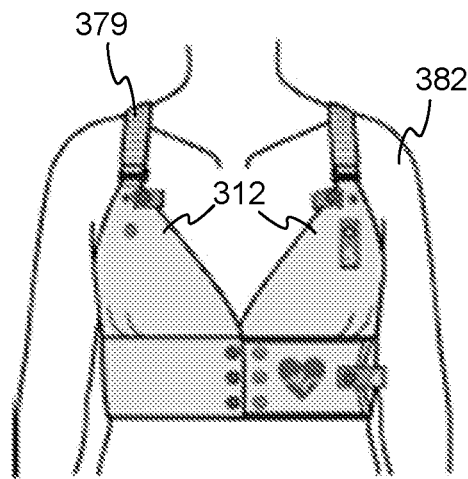
FIG. 3 is a diagram showing a partial front view of another patient wearing a sample garment embodiment of an alternate style as worn by a patient, and which can be a support structure of a WMS that implements a WCD such as that of FIG. 1.

FIG. 3 is a diagram showing a partial front view of another patient 382 wearing another garment 379. The garment 379 is of an alternate style than the garment 279, in that it further includes breast support receptacles 312, as was described for instance in U.S. Pat. No. 10,926,080. This style of garment may be more comfortable if the patient 382 is a woman.

Figure 4:
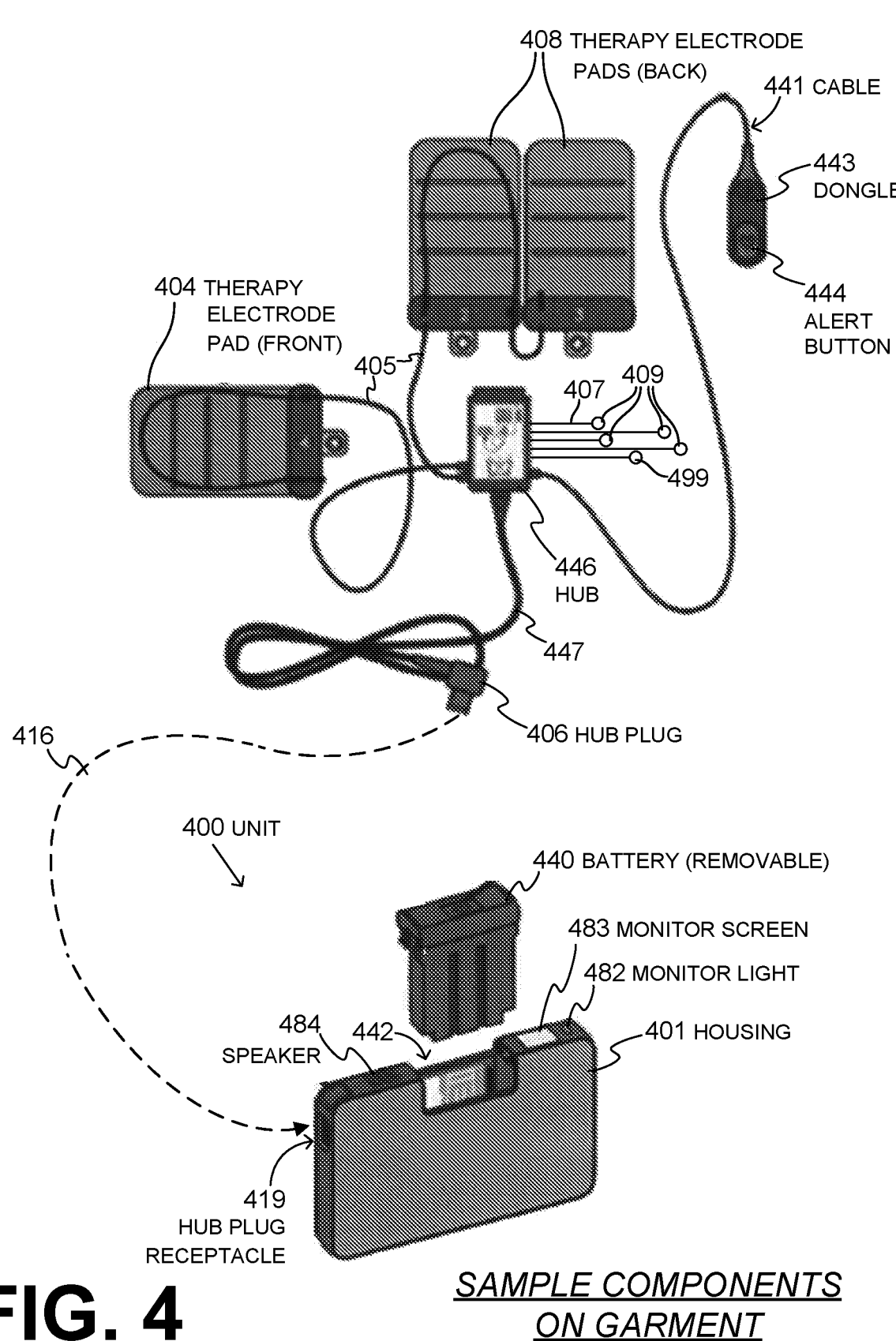
FIG. 4 is a diagram showing sample embodiments of electronic components of a WMS that implements a WCD, and which can be used with the garment of FIG. 2A or of FIG. 3.

FIG. 4 shows sample electronic components that can be used with the garments 279, 379. The components of FIG. 4 include a unit 400, shown at the lower portion of FIG. 4. The unit 400 includes a housing 401, and a hub plug receptacle 419 at the housing 401.

The unit 400 includes a battery opening 442 at the housing 401. The battery opening 442 is configured to receive a removable battery 440. A system according to embodiments can have two identical such batteries 440, one plugged into the housing 401 while another one (not shown) is being charged by a charger (not shown). The batteries can then be interchanged when needed.

The unit 400 also includes devices for implementing a user interface. In this example, these devices include a monitor light 482, a monitor screen 483 and a speaker 484. Additional devices may include a vibrating mechanism, and so on.

The unit 400 can implement many of the functions of the unit 100 of FIG. 1. In the embodiment of FIG. 4, however, some of the functions of the unit 100 are implemented instead by a separate hub 446, which can be connected to the unit 400. The hub 446 is smaller and lighter than the unit 400, and can accommodate multiple electrical connections to other components of FIG. 4. A cable 447, similar to the cable 247 of FIG. 2D, emerges from the hub 446 and terminates in a hub plug 406. The hub plug 406 can be plugged into the hub plug receptacle 419 of the unit 400 according to an arrow 416.

ECG sensing electrodes 409, 499, plus their wires or leads 407 are further shown conceptually in FIG. 4 for completeness. The wires or leads 407 that can be configured to be coupled to the hub 446.

The components of FIG. 4 also include the therapy electrode pads 404, 408. The therapy electrode pad 404 can be inserted into the pocket 204 of FIG. 2B, while the therapy electrode pads 408 can be inserted into the pockets 208 of FIG. 2B. The shock is generated between the therapy electrode pad 404 and the therapy electrode pads 408 taken together. Indeed, the therapy electrode pads 408 are electrically connected to each other. The therapy electrode pads 404, 408, have leads 405, which can be configured to be coupled to the hub 446.

The components of FIG. 4 further include a dongle 443 with a cable 441. The dongle 443 can be configured to be coupled to the hub 446 via a cable 441. In other embodiments, the dongle 443 can be configured to be coupled directly to the unit 400.

An alert button 444 is on the dongle 443. The cable 441 includes the wires necessary to couple electrically the alert button 444 to, ultimately, the processor in the unit 400. The alert button 444 can be used by the patient to give emergency input to the WMS. For instance, the alert button 444 can be the cancel switch, namely what the patient uses to notify the system that the patient is actually alive and an imminent shock is not actually needed, which may otherwise happen in the event of a false positive detection of a shockable heart rhythm of the patient. The button 444 may have additional uses.

Figure 5:
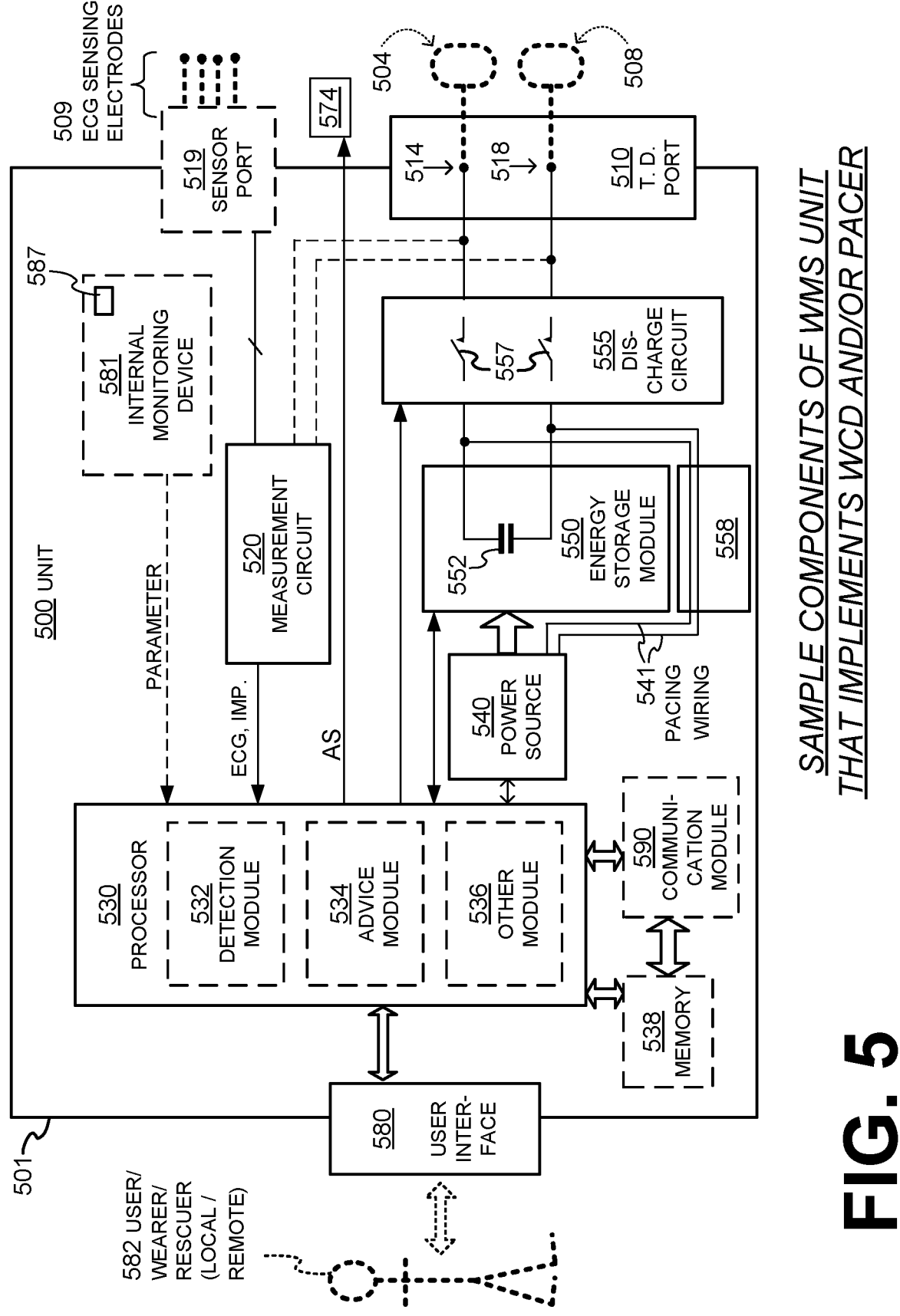
FIG. 5 is a diagram showing sample components of a unit of FIG. 1, which is made according to embodiments.

FIG. 5 shows a sample unit 500, which could be the unit 100 of FIG. 1. The unit 500 implements an external defibrillator and/or a pacer. The sample unit 500 thus combines the functions of the unit 400 and of the hub 446 of FIG. 4. The components shown in FIG. 5 can be provided in a housing 501, which may also be referred to as casing 501.

The unit 500 may include a user interface (UI) 580 for a user 582. User 582 can be the patient 82, also known as patient 582, also known as the wearer 582. Or, the user 582 can be a local rescuer at the scene, such as a bystander who might offer assistance, or a trained person. Or, the user 582 might be a remotely located trained caregiver in communication with the WMS, such as a clinician.

The user interface 580 can be made in a number of ways. The user interface 580 may include output devices, which can be visual, audible or tactile, for communicating to a user by outputting images, sounds or vibrations. Images, sounds, vibrations, and anything that can be perceived by user 582 can also be called human-perceptible indications. As such, an output device according to embodiments can be configured to output a human-perceptible indication (HPI). Such HPIs can be used to alert the patient, sound alarms that may be intended also for bystanders, and so on. There are many instances of output devices. For example, an output device can be a light that can be turned on and off, a screen to display what is sensed, detected and/or measured, and provide visual feedback to the local rescuer 582 for their resuscitation attempts, and so on. Another output device can be a speaker, which can be configured to issue voice prompts, alerts, beeps, loud alarm sounds and/or words, and so on. These can also be for bystanders, when defibrillating or just pacing, and so on. Examples of output devices were the monitor light 482, the monitor screen 483 and the speaker 484 of the unit 400 seen in FIG. 4.

The user interface 580 may further include input devices for receiving inputs from users. Such users can be the patient 82, 582, perhaps a local trained caregiver or a bystander, and so on. Such input devices may include various controls, such as pushbuttons, keyboards, touchscreens, one or more microphones, and so on. As will be understood, in some embodiments the microphone 176 is part of the UI 580.

An input device can be a cancel switch, which is sometimes called an "I am alive" switch or "live man" switch. The cancel switch can be configured to be actuated by the patient. In some embodiments, actuating the cancel switch can prevent the impending delivery of a shock, or of pacing pulses. An example of a cancel switch was the alert button 444 seen in FIG. 4.

In particular, in some embodiments the processor 530 can cause an output device that is configured to output a human-perceptible warning prompt to actually output such as human-perceptible warning prompt, as a result of determining from the patient input that a shock criterion is met. This prompt can be caused to be output prior to actually delivering the shock, whether that is a defibrillation shock or a pacing sequence of pacing pulses. Then the processor 530 can be configured to wait for a preset amount of time, for the event that the ambulatory patient 82 actuates the cancel switch in the interim, in response to the warning prompt being output. In such embodiments, the processor 530 can cause the shock to be delivered if the cancel switch has not been actuated during the preset amount of time, but, if the cancel switch has been actuated by the patient during the preset amount of time, the processor 530 can be configured to not cause any of the stored electrical charge to be thus discharged responsive to the shock criterion being met.

The unit 500 may include an internal monitoring device 581. The device 581 is called an "internal" device because it is incorporated within the housing 501. The monitoring device 581 can sense or monitor patient parameters such as patient physiological parameters, system parameters and/or environmental parameters, all of which can be called patient data. In other words, the internal monitoring device 581 can be complementary of, or an alternative to, the outside monitoring device 180 of FIG. 1. Allocating which of the parameters are to be monitored by which of the monitoring devices 180, 581 can be done according to design considerations. The device 581 may include one or more sensors, as also described elsewhere in this document.

Patient parameters may include patient physiological parameters. Patient physiological parameters may include, for example and without limitation, those physiological parameters that can be of any help in detecting by the WMS whether or not the patient is in need of a shock or other intervention or assistance. Patient physiological parameters may also optionally include the patient's medical history, event history and so on. Examples of such parameters include the above-described electrodes to detect the ECG, blood oxygen level, blood flow, blood pressure, blood perfusion, pulsatile change in light transmission or reflection properties of perfused tissue, heart sounds, heart wall motion, breathing sounds and pulse. Accordingly, the monitoring devices 180, 581 may include one or more sensors or transducers configured to acquire patient physiological signals. Examples of such sensors and transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter reflects a trend that can be detected in a monitored physiological parameter of the patient 82, 582. Such a trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of the patient 82, 582 will know about a condition that is either not improving or deteriorating.

Patient state parameters include recorded aspects of the patient 582, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed of the patient can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WMS made according to embodiments may thus include a motion detector. In embodiments, a motion detector can be implemented within the outside monitoring device 180 or within the internal monitoring device 581. A motion detector of a WMS according to embodiments can be configured to detect a motion event. A motion event can be defined as is convenient, for example a change in posture or motion from a baseline posture or motion, etc. In such cases, a sensed patient parameter is motion. Such a motion detector can be made in many ways as is known in the art, for example by using an accelerometer and so on. In this example, a motion detector 587 is implemented within the monitoring device 581.

System parameters of a WMS can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if the monitoring device 180 or 581 includes a GPS location sensor as per the above, and if it is presumed or sensed that the patient is wearing the WMS.

The unit 500 includes a therapy delivery port 510 and a sensor port 519 in the housing 501. In contrast, in FIG. 4 these ports are located at the hub 446.

In FIG. 5, the therapy delivery port 510 can be a socket in the housing 501, or other equivalent structure. The therapy delivery port 510 includes electrical nodes 514, 518. Therapy electrodes 504, 508 are shown, which can be as the therapy electrodes 104, 108. Leads of the therapy electrodes 504, 508, such as the leads 105 of FIG. 1, can be plugged into the therapy delivery port 510, so as to make electrical contact with the nodes 514, 518, respectively. It is also possible that the therapy electrodes 504, 508 are connected continuously to the therapy delivery port 510, instead. Either way, the therapy delivery port 510 can be used for guiding, via electrodes, to the wearer at least some of the electrical charge that has been stored in an energy storage module 550 that is described more fully later in this document. When thus guided, the electric charge will cause the shock 111 to be delivered.

The sensor port 519 is also in the housing 501, and is also sometimes known as an ECG port. The sensor port 519 can be adapted for plugging in the leads of ECG sensing electrodes 509. The ECG sensing electrodes 509 can be as the ECG sensing electrodes 209. The ECG sensing electrodes 509 in this example are distinct from the therapy electrodes 504, 508. It is also possible that the sensing electrodes 509 can be connected continuously to the sensor port 519, instead. The electrodes 509 can be types of transducers that can help sense an ECG signal of the patient, e.g. a 12-lead signal, or a signal from a different number of leads, especially if they make good electrical contact with the body of the patient and in particular with the skin of the patient. As with the therapy electrodes 504, 508, the support structure can be configured to be worn by the patient 582 so as to maintain the sensing electrodes 509 on a body of the patient 582. For example, the sensing electrodes 509 can be attached to the inside of the support structure 170 for making good electrical contact with the patient, similarly with the therapy electrodes 504, 508.

Optionally a WMS according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel. As such, it will not flow too far away from the location it is released. The fluid can be used for both the therapy electrodes 504, 508, and for the sensing electrodes 509.

The fluid may be initially stored in a fluid reservoir, not shown in FIG. 5. Such a fluid reservoir can be coupled to the support structure. In addition, a WMS according to embodiments further includes a fluid deploying mechanism 574. The fluid deploying mechanism 574 can be configured to cause at least some of the fluid to be released from the reservoir, and be deployed near one or both of the patient body locations to which the therapy electrodes 504, 508 are configured to be attached to the patient's body. In some embodiments, the fluid deploying mechanism 574 is activated prior to the electrical discharge responsive to receiving an activation signal AS from the processor 530, which is described more fully later in this document.

In some embodiments, the unit 500 also includes a measurement circuit 520, as one or more of its modules working together with its sensors and/or transducers. The measurement circuit 520 senses one or more electrical physiological signals of the patient from the sensor port 519, if provided. Even if the unit 500 lacks a sensor port, the measurement circuit 520 may optionally obtain physiological signals through the nodes 514, 518 instead, when the therapy electrodes 504, 508 are attached to the patient. In these cases, the input reflects an ECG measurement. The patient parameter can be an ECG, which can be sensed as a voltage difference between electrodes 504, 508. In addition, the patient parameter can be an impedance (IMP. or Z), which can be sensed between the electrodes 504, 508 and/or between the connections of the sensor port 519 considered pairwise as channels. Sensing the impedance can be useful for detecting, among other things, whether these electrodes 504, 508 and/or the sensing electrodes 509 are not making good electrical contact with the patient's body at the time. These patient physiological signals may be sensed when available. The measurement circuit 520 can then render or generate information about them as inputs, data, other signals, etc. As such, the measurement circuit 520 can be configured to render a patient input responsive to a patient parameter sensed by a sensor. In some embodiments, the measurement circuit 520 can be configured to render a patient input, such as values of an ECG signal, responsive to the ECG signal sensed by the ECG sensing electrodes 509. More strictly speaking, the information rendered by the measurement circuit 520 is output from it, but this information can be called an input because it is received as an input by a subsequent stage, device or functionality.

The unit 500 also includes a processor 530. The processor 530 may be implemented in a number of ways. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 530 may include, or have access to, a non-transitory storage medium, such as a memory 538 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

The processor 530 can be considered to have a number of modules. One such module can be a detection module 532. The detection module 532 can include a Ventricular Fibrillation (VF) detector. The patient's sensed ECG from measurement circuit 520, which can be available as inputs, data that reflect values, or values of other signals, may be used by the VF detector to determine whether the patient is experiencing VF. Detecting VF is useful, because VF typically results in SCA. The detection module 532 can also include a Ventricular Tachycardia (VT) detector for detecting VT, and so on.

Another such module in processor 530 can be an advice module 534, which generates advice for what to do. The advice can be based on outputs of the detection module 532. There can be many types of advice according to embodiments. In some embodiments, the advice is a shock/no shock determination that processor 530 can make, for example via advice module 534. The shock/no shock determination can be made by executing a stored Shock Advisory Algorithm. A Shock Advisory Algorithm can make a shock/no shock determination from one or more ECG signals that are sensed according to embodiments, and determine whether or not a shock criterion is met. The determination can be made from a rhythm analysis of the sensed ECG signal or otherwise. For example, there can be shock decisions for VF, VT, etc.

In perfect conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in published US patent application No. US 2019/0030351 A1, and No. US 2019/0030352 A1, and which are incorporated herein by reference.

The processor 530 can include additional modules, such as other module 536, for other functions. In addition, if the internal monitoring device 581 is indeed provided, the processor 530 may receive its inputs, etc.

The unit 500 optionally further includes a memory 538, which can work together with the processor 530. The memory 538 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. The memory 538 is thus a non-transitory storage medium. The memory 538, if provided, can include programs for the processor 530, which the processor 530 may be able to read and execute. More particularly, the programs can include sets of instructions in the form of code, which the processor 530 may be able to execute upon reading. Executing is performed by physical manipulations of physical quantities, and may result in functions, operations, processes, acts, actions and/or methods to be performed, and/or the processor 530 to cause other devices or components or blocks to perform such functions, operations, processes, acts, actions and/or methods. The programs can be operational for the inherent needs of the processor 530, and can also include protocols and ways that decisions can be made by the advice module 534. In addition, the memory 538 can store prompts for the user 582, if this user is a local rescuer. Moreover, the memory 538 can store data. This data can include patient data, system data and environmental data, for example as learned by the internal monitoring device 581 and the outside monitoring device 180. The data can be stored in the memory 538 before it is transmitted out of the unit 500, or be stored there after it is received by the unit 500.

The unit 500 can optionally include a communication module 590, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, the communication module 590 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. The module 590 may also include such interconnected sub-components as may be deemed necessary by a person skilled in the art, for example an antenna, portions of a processor, supporting electronics, outlet for a telephone or a network cable, etc.

The unit 500 may also include a power source 540, which is configured to provide electrical charge in the form of a current. To enable portability of the unit 500, the power source 540 typically includes a battery. Such a battery is typically implemented as a battery pack, which can be rechargeable or not. Sometimes a combination is used of rechargeable and non-rechargeable battery packs. An example of a rechargeable battery 540 was a battery 440 of FIG. 4. Other embodiments of the power source 540 can include an AC power override, for where AC power will be available, an energy-storing capacitor, and so on. Appropriate components may be included to provide for charging or replacing the power source 540. In some embodiments, the power source 540 is controlled and/or monitored by the processor 530.

The unit 500 may additionally include an energy storage module 550. The energy storage module 550 can be coupled to receive the electrical charge provided by the power source 540. The energy storage module 550 can be configured to store the electrical charge received by the power source 540. As such, the energy storage module 550 is where some electrical energy can be stored temporarily in the form of an electrical charge, when preparing it for discharge to administer a shock. In embodiments, the module 550 can be charged from the power source 540 to the desired amount of energy, for instance as controlled by the processor 530. In typical implementations, the module 550 includes a capacitor 552, which can be a single capacitor or a system of capacitors, and so on. In some embodiments, the energy storage module 550 includes a device that exhibits high power density, such as an ultracapacitor. As described above, the capacitor 552 can store the energy in the form of an electrical charge, for delivering to the patient.

As mentioned above, the patient is typically shocked when the shock criterion is met. In particular, in some embodiments the processor 530 is configured to determine from the patient input whether or not a shock criterion is met, and cause, responsive to the shock criterion being met, at least some of the electrical charge stored in the module 550 to be discharged via the therapy electrodes 104, 108 through the ambulatory patient 82 while the support structure is worn by the ambulatory patient 82 so as to deliver the shock 111 to the ambulatory patient 82. Delivering the electrical charge is also known as discharging and shocking the patient.

For causing the discharge, the unit 500 moreover includes a discharge circuit 555. When the decision is to shock, the processor 530 can be configured to control the discharge circuit 555 to discharge through the patient at least some of all of the electrical charge stored in the energy storage module 550, especially in a desired waveform. When the decision is to merely pace, i.e., to deliver pacing pulses, the processor 530 can be configured to cause control the discharge circuit 555 to discharge through the patient at least some of the electrical charge provided by the power source 540. Since pacing requires lesser charge and/or energy than a defibrillation shock, in some embodiments pacing wiring 541 is provided from the power source 540 to the discharge circuit 555. The pacing wiring 541 is shown as two wires that bypass the energy storage module 550, and only go through a current-supplying circuit 558. As such, the energy for the pacing is provided by the power source 540 either via the pacing wiring 541, or through the energy storage module 550. And, in some embodiments where only a pacer is provided, the energy storage module 550 may not be needed if enough pacing current can be provided from the power source 540. Either way, discharging can be to the nodes 514, 518, and from there to the therapy electrodes 504, 508, so as to cause a shock to be delivered to the patient. The circuit 555 can include one or more switches 557. The switches 557 can be made in a number of ways, such as by an H-bridge, and so on. In some embodiments, different ones of the switches 557 may be used for a discharge where a defibrillation shock is caused to be delivered, than for a discharge where the much weaker pacing pulses are caused to be delivered. The circuit 555 could also be thus controlled via the processor 530, and/or the user interface 580.

The pacing capability can be implemented in a number of ways. ECG sensing may be done in the processor, as mentioned elsewhere in this document, or separately, for demand or synchronous pacing. In some embodiments, however, pacing can be asynchronous. Pacing can be software controlled, e.g., by managing the defibrillation path, or a separate pacing therapy circuit (not shown) could be included, which can receive the ECG sensing, via the circuit 520 or otherwise.

A time waveform of the discharge may be controlled by thus controlling discharge circuit 555. The amount of energy of the discharge can be controlled by how much energy storage module has been charged, and also by how long the discharge circuit 555 is controlled to remain open.

The unit 500 can optionally include other components.

In embodiments, the shock/no shock decision can be made from the patient's heart rate and/or the QRS width of the patient's ECG complexes in the patient's ECG signal. Other parameters may also be used, such as information from a patient impedance signal (Z), information from a motion detection signal (MDET) that may evidence a motion of the patient, and so on. Of course, it is desired to measure these parameters as accurately as possible.

Returning to FIG. 1, the components 199 further include a microphone 176. In embodiments, the microphone 176 is configured to capture ambient sounds 165, which include sounds, noise, voices, and so on. The microphone 176 can be further configured to output an audio signal 177 responsive to the ambient sounds 165. The audio signal 177 can be routed according to an arrow 178, which can be a conductor for a signal, a path for data, and so on as is described later in embodiments.

The microphone 176 can be placed at a number of locations, within the WMS. For instance, it may be placed on the unit 100. Or it may be the microphone of a related device, such as a peripheral device that is used in combination with the WMS. Such a peripheral device can be a custom electronic device, or a general-purpose electronic device with a custom software application, such as a tablet, a smartphone and the like.

In embodiments, the microphone is on the same dongle as the cancel switch. Examples are now described.

Figure 6:
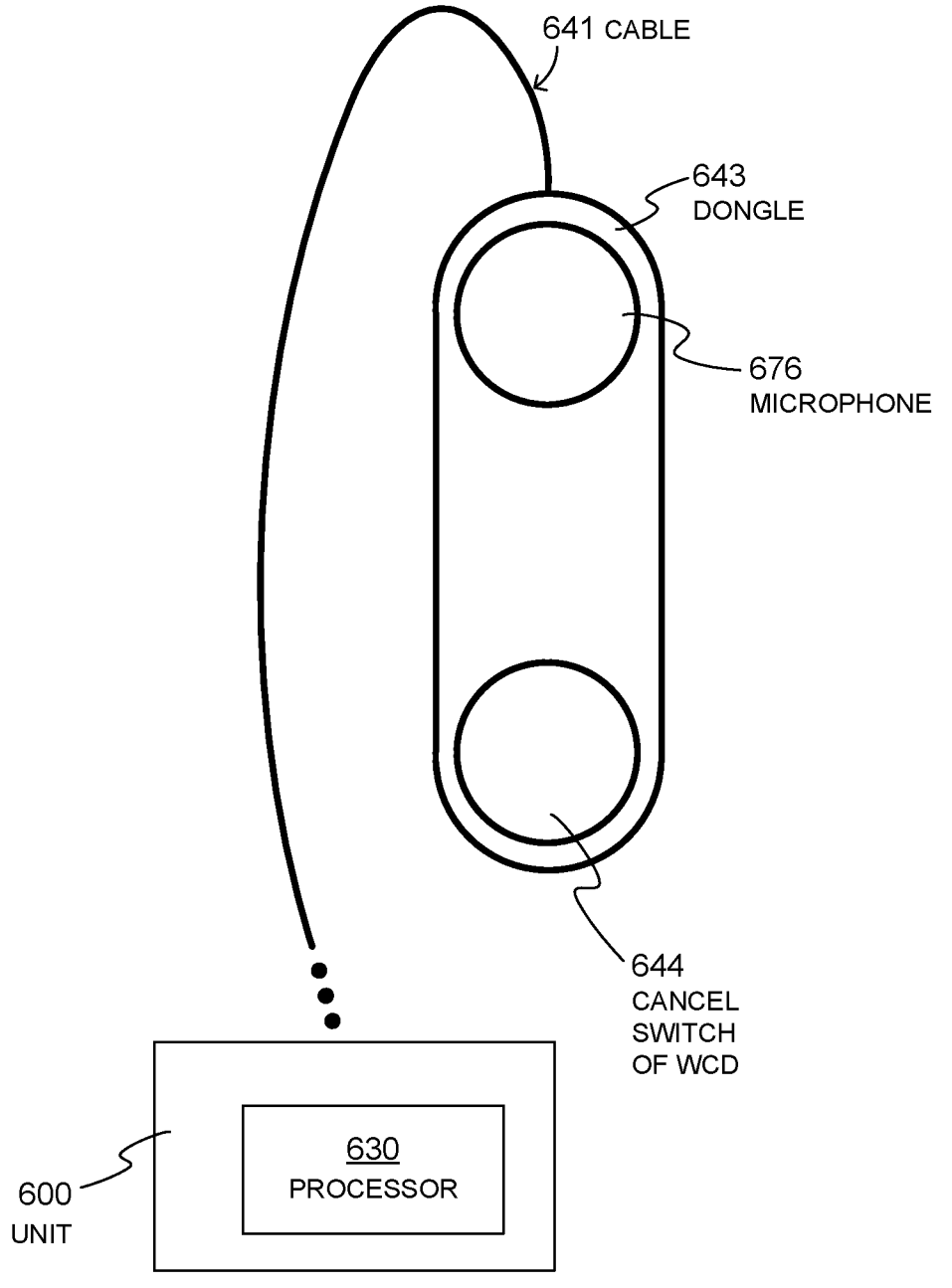
FIG. 6 is a diagram of sample embodiments where the microphone is hosted on the same dongle as the cancel switch.

FIG. 6 is a diagram of a dongle 643 that has a cable 641. A cancel switch 644 of a WCD is on the dongle 643. A microphone 676 is located also on the dongle 643.

The cable 641 has wires inside (note shown), which are ultimately electrically coupled to a unit 600 that has a processor 630. The word "ultimately" is written because the coupling can be indirect, via a hub, as in FIG. 4, or direct; and the dot-dot-dot is shown to encompass both types of embodiments. The unit 600 can be like the unit 400, or the unit 100, and so on. With such coupling of the microphone 676, the audio signal is routed via at least one of the wires that is in the cable 641. An efficiency of the microphone's placement on the dongle 643 is that the wires for the microphone's audio signal can be located within the already-provided cable 641, and thus no separate cable is required when adding the microphone 676 to the dongle 643, as opposed to having the microphone 676 elsewhere closer to the mouth of the patient and away from the unit 600.

In embodiments, the dongle 643 is configured to be supportable by the support structure 170. For instance, clasps may secure the dongle 643, directly or by its cable 641, to a location suitable for the patient to find it easily in an emergency. One such location is on the chest of the patient 82, so that the patient 82 can access it quickly.

The dongle may further include additional UI devices, such as a speaker and/or a vibration mechanism. Examples are now described, some of which can be implemented as described for similar elements in FIG. 6.

Figure 7:
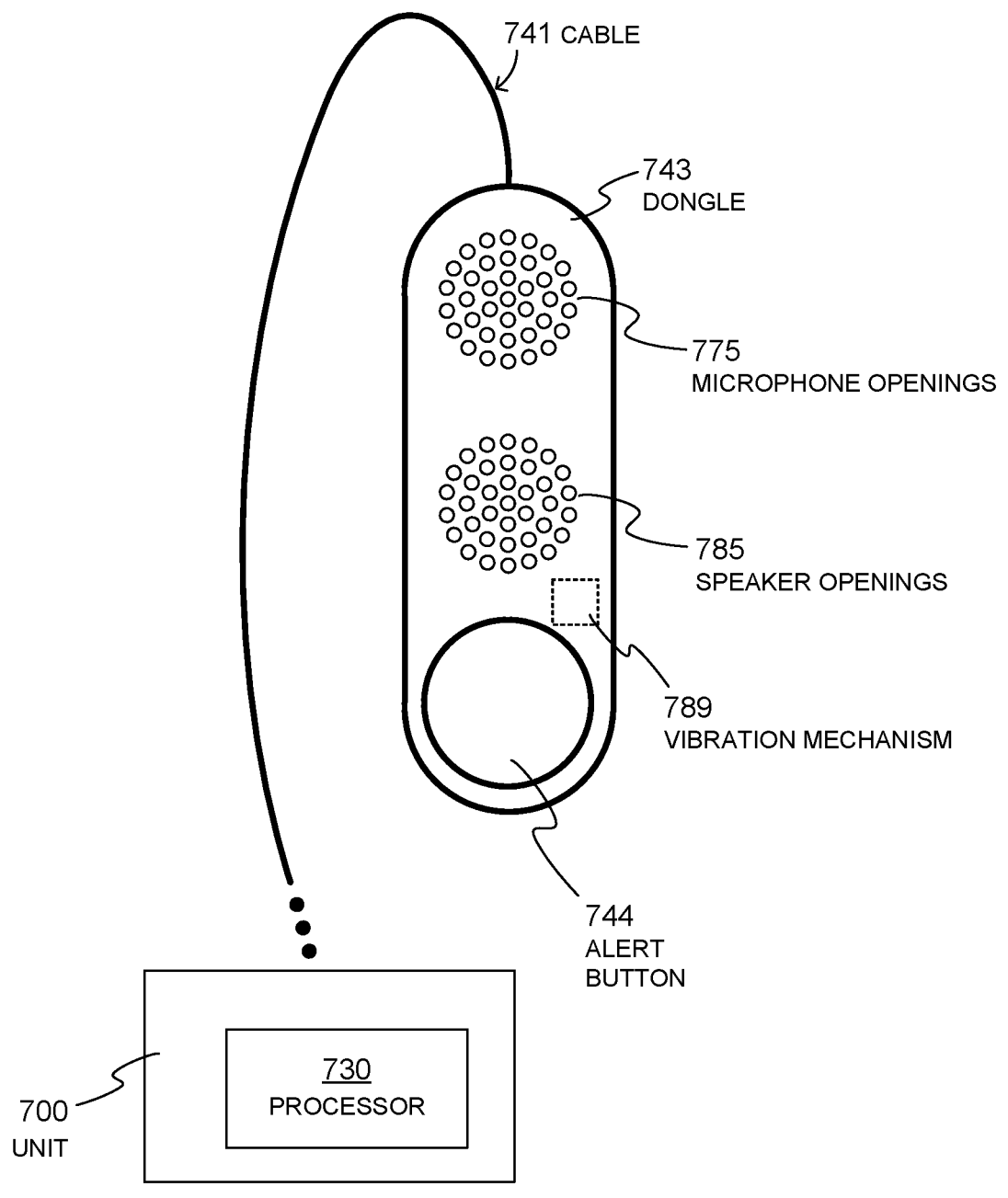
FIG. 7 is a diagram of a sample implementation of the embodiments of FIG. 6.

FIG. 7 shows a sample implementation a dongle 743 that has a cable 741. The cable 741 has wires inside that are configured to be ultimately electrically coupled to a unit 700 and to a processor 730. The dongle 743 may be made from a suitable material, such as hard plastic.

The dongle 743 has on it an alert button 744. The alert button 744 operates as the cancel switch 644, and may have additional uses.

In this example, a microphone (not shown) is located within the dongle 743. On the surface of the dongle 743 are microphone openings 775, to permit the microphone to capture the ambient sounds 165.

In this example, a speaker (not shown) is located within the dongle 743. On the surface of the dongle 743 are speaker openings 785, to permit sounds by the speaker to be heard by the patient and perhaps any bystanders.

In this example, a vibration mechanism 789 is located within the dongle 743. The vibration mechanism 789 may vibrate to give a signal to the patient, in what is called a haptic user interface.

Returning to FIG. 1, in embodiments, the audio signal 177 is routed according to the arrow 178 to a memory 138, for recording in the memory 138 audio data from the audio signal 177. The memory 138 shown in FIG. 1 could be the memory 538 that may be in the unit 100, as indicated by bent lines to the unit 100, or it could be the memory of a different, peripheral device associated with the WMS. In embodiments, the memory 138 is a non-transitory computer-readable medium storing one or more programs which can be executed by one or more processors of the WMS. When so executed, these one or more programs result in operations that are described in this document. For the recording, one or more processors may be involved in the WMS, in the unit 100 and/or any peripheral devices. The one or more processors may control the one or more memories so that they may cause audio data to be recorded in the one or more memories responsive to the audio signal 177.

In some embodiments, the audio recording can be selectively initiated by the patient 82 performing a deliberate action. This feature is depicted in FIG. 1 by including, among the components 199, an optional electrical switch 179 near the arrow 178. In this metaphor, the deliberate action of the patient 82 to initiate the recording would be to "turn on" the switch 179, so that audio signal 177 can start reaching the memory 138. In terms of electrical engineering, this action would be called to "close" the switch 179. And, of course engineering implementations may be also depicted by logical means, for instance the switch 179 can be a flag that is set or not set, a state of a state machine, and so on, all of which are ultimately implemented by electrical components. Examples are now described.

Figure 8:
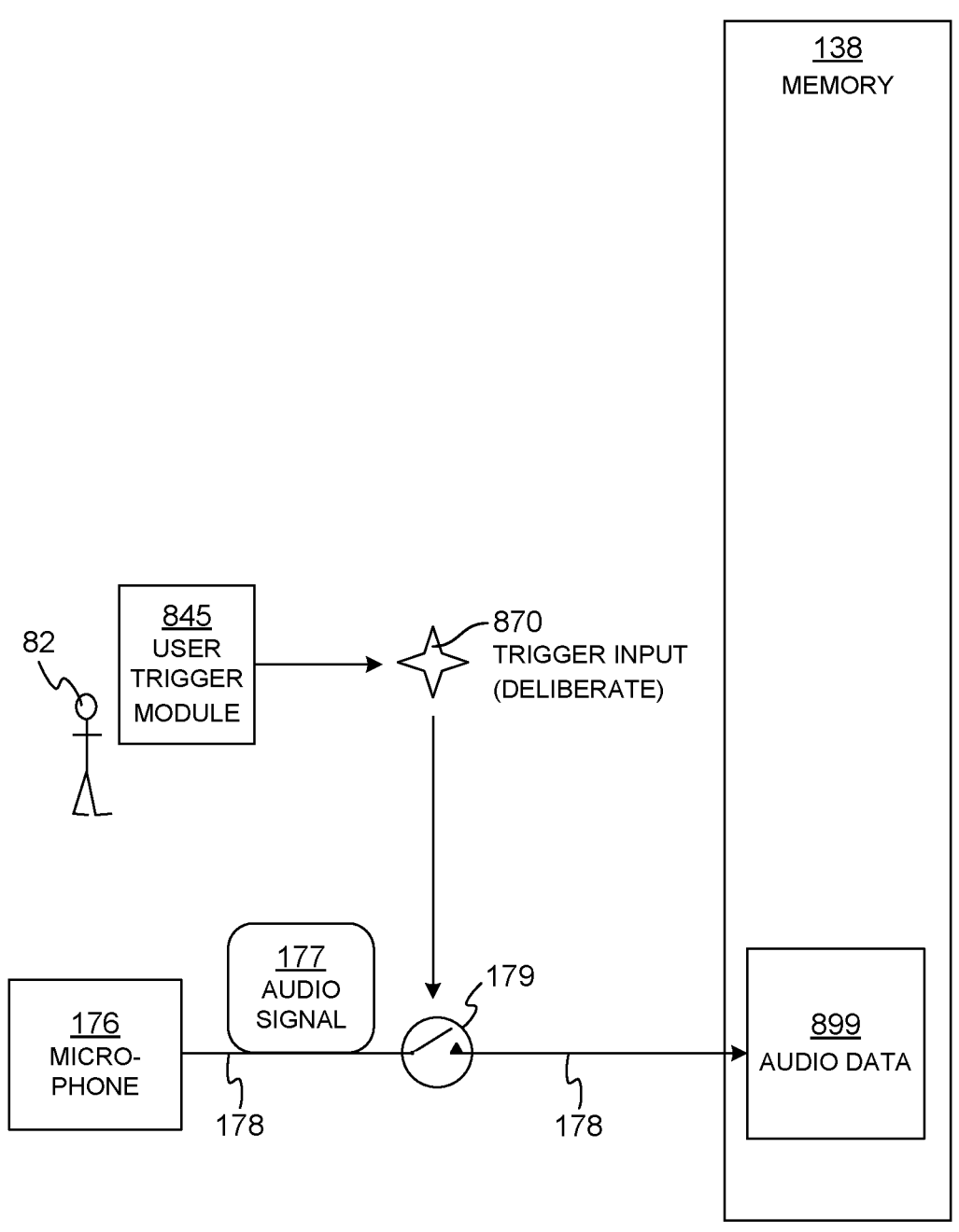
FIG. 8 is a diagram showing sample components where a user trigger module is used to start recording audio data in a memory, according to embodiments.

FIG. 8 shows the microphone 176, the audio signal 177, the arrow 178, the switch 179 and the memory 138 of FIG. 1. The arrow 178 is interrupted by the switch 179. When the switch 179 is closed, audio data 899 is caused to be recorded in the memory 138 responsive to the audio signal 177.

In some embodiments, the WMS also includes a user trigger module 845, which can be implemented as described later in this document. The user trigger module 845 can be configured to enable the patient 82 to deliberately generate a trigger input 870. The trigger input 870 can be implemented in a number of ways, such as setting or unsetting flag, changing a state of a state machine, and so on.

In such embodiments, the one or more processors can be programmed to detect the deliberately generated trigger input 870, and to start, responsive to the detected trigger input 870, causing the audio data 899 to be recorded in the memory 138 responsive to the received audio signal 177. This is depicted metaphorically in FIG. 8 by an arrow from the trigger input 870 to control the switch 179, namely to close it for starting the recording. Of course, it will be recognized that the audio signal 177 may initially be an analog signal, and it could become digitized into the audio data 899 at some point.

The devices and/or systems mentioned in this document may perform functions, processes, acts, operations, actions and/or methods. These functions, processes, acts, operations, actions and/or methods may be implemented by one or more devices that include logic circuitry. A single such device can be alternately called a computer, and so on. It may be a standalone device or computer, such as a general-purpose computer, or part of a device that has and/or can perform one or more additional functions. The logic circuitry may include one or more processors and non-transitory computer-readable storage media, such as memories, of the type described elsewhere in this document. These can be configured to or designed to or programmed to perform operations. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description may include flowcharts, display images, algorithms, and symbolic representations of program operations within at least one computer readable medium. An economy may be achieved in that a single set of flowcharts can be used to describe both programs, and also methods. So, while flowcharts describe methods in terms of boxes, they may also concurrently describe programs.

Methods are now described.

Figure 9:
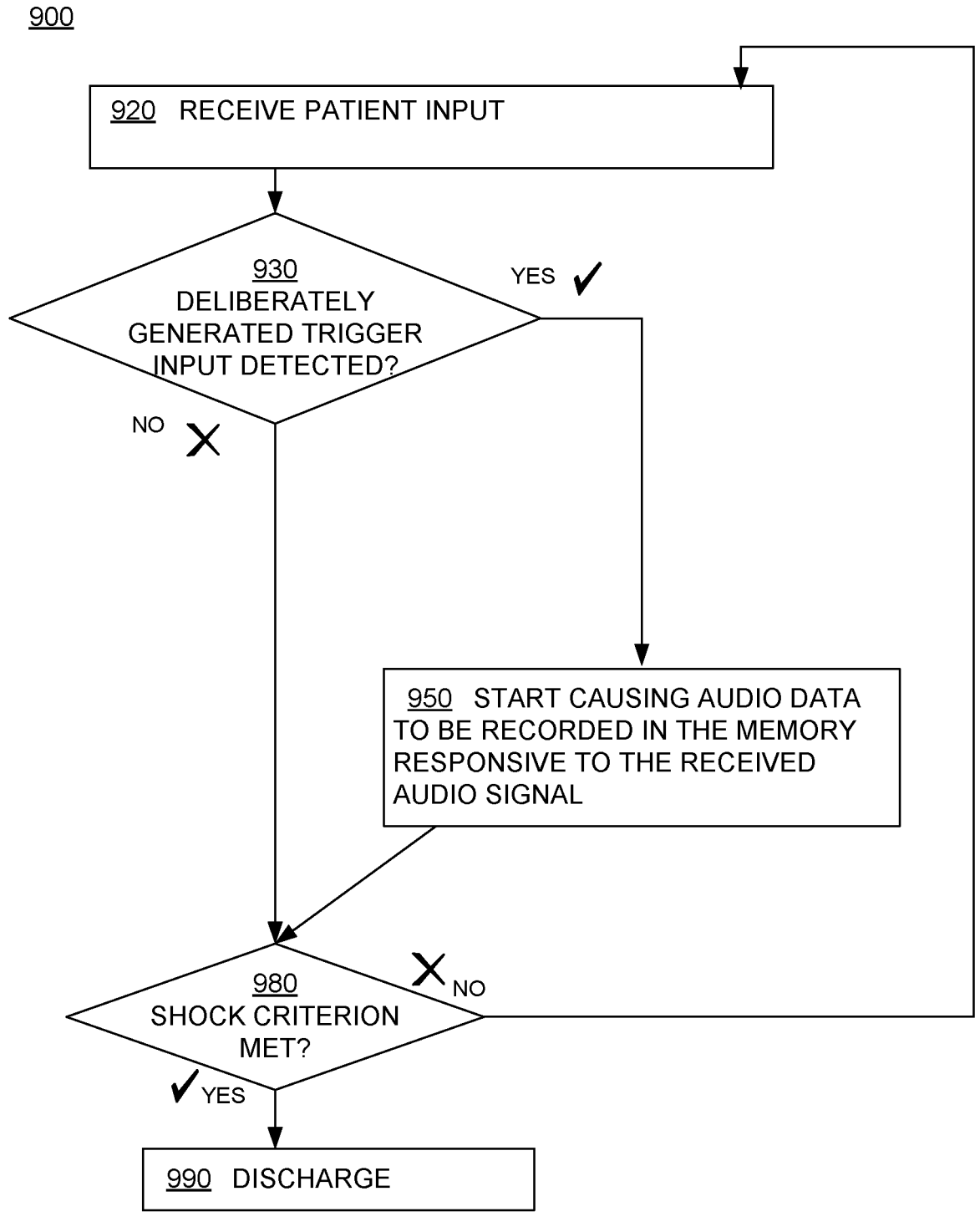
FIG. 9 is a flowchart for illustrating sample methods according to embodiments.

FIG. 9 shows a flowchart 900 for describing methods for starting an audio recording according to embodiments.

According to an operation 920, the patient input may be received, for example by the one or more processors.

According to another operation 930, it may be determined whether or not a deliberately generated trigger input was detected. Th trigger input could have been generated by the patient 82 actuating the user trigger module 845. If yes, then according to another operation 950, audio data may start to be caused to be recorded in the memory, responsive to the trigger input being detected and responsive to the received audio signal.

After the operation 950, or if the answer to the operation 930 is no, then according to another operation 980, it can be determined from the patient input whether or not a shock criterion is met. If no, execution may return to the operation 920, or to another operation to determine whether any started recording is to be stopped, as described further below.

If the answer to the operation 980 is yes then, according to another operation 990, at least some of the stored electrical charge can be caused to be discharged via a therapy electrode through the ambulatory patient 82, while the support structure is worn by the ambulatory patient 82, so as to deliver a shock to the ambulatory patient 82. After that, execution may return to the operation 920.

It will be appreciated that the above can start a recording. In such embodiments, the one or more processors can be further programmed to stop the recording in the memory, responsive to a stop audio recording event occurring. The stop audio recording event may be implemented in a number of ways. For instance, the stop audio recording event can be the passage of a predetermined amount of time from when the deliberately generated trigger input was detected. Or, it can be the detection of another deliberately generated trigger input, of the same or different type than the trigger input 870, such as a suitable voice command, as will be understood from the below. Or, it can be the passage of a predetermined amount of time from when a recording condition ends, such as an ECG episode ending, the cancel switch being released, or other variable changes. It will be observed that the different possible stop audio recording events could result in recordings of different durations. An example is now described.

Figure 10:
FIG. 10 is a timing diagram showing sample durations of audio data recordings resulting from deliberate recording triggers by the patient, according to embodiments.

FIG. 10 shows a timing diagram 1000. A time axis 1008 shows sample time moments 1040, 1042, 1043, 1045, 1046. A block 1065 represents ambient sounds at various times, at least from the time moment 1040 to the time moment 1046.

A group 1070 shows deliberate recording trigger inputs that are detected by the processor. The group 1070 includes a trigger input 1071, detected at the time moment 1042, and a trigger input 1072, detected at the time moment 1045.

A group 1090 shows sound recordings that are made as a result of the recording trigger inputs of the group 1070. The group 1090 includes a recording 1091, which starts at the time moment 1042 and ends at the time moment 1043. Therefore, the recording 1091 captures a portion 1061A of the ambient sounds 1065. The group 1090 also includes a recording 1092, which starts at the time moment 1045 and ends at the time moment 1046. Therefore, the recording 1092 captures a portion 1062A of the ambient sounds 1065. It will be observed that the recording 1092 is longer, in this example, than the recording 1091.

It will be understood that only snippets of the ambient sounds 1065 may be captured that way. Of course that would be because the non-captured of the ambient sounds 1065 are not interesting for study, and memory can thus be conserved.

In some embodiments, ECG recording in the WMS can be selectively initiated by the patient 82 performing a deliberate action. Ordinarily, not all values of the ECG signal are recorded, first because they are very many, and second because they are not interesting. Embodiments, however, enable the patient 82 to cause the system to start recording their ECG. Examples are now described.

FIG. 11 shows again the memory 138, and a measurement circuit 1120 that can be as the measurement circuit 520. The measurement circuit 1120 receives the ECG signal 1121. In such embodiments, the WMS also includes a user trigger module 1145, which can be implemented as described later in this document. The user trigger module 1145 can be configured to enable the patient 82 to deliberately generate a trigger input 1170. The user trigger module 1145 can be different than, or the same as, the user trigger module 845.

In such embodiments, the one or more processors can be programmed to detect the deliberately generated trigger input 1170, and to start, responsive to the detected trigger input 1170, causing at least some of the values 1198 of the ECG signal 1121 to be recorded in the memory 138. This is depicted metaphorically in FIG. 11 by an arrow from the trigger input 1170 to control a switch 1129, namely to close it for starting the recording. Of course, it will be recognized that the ECG signal 1121 may initially be an analog signal, and it may become digitized into the ECG signal values 1198 at some point. The switch 1129 can be made as described for the switch 179 with the suitable adaptations, and so on.

Some of these embodiments do not necessarily need the microphone 176.

Optionally only, if the microphone 176 is indeed provided, when the user initiates recording of ECG signal values, some of these embodiments may further initiate audio recording as described above. For such optional embodiments, FIG. 11 further repeats the microphone 176, the audio signal 177, the arrow 178, and the switch 179 of FIG. 1, and also of FIG. 8. The switch 179 can be closed by the trigger input 1170, which then causes audio data 1199 to be recorded in the memory 138 responsive to the audio signal 177.

FIG. 12 shows a flowchart 1200 for describing methods for starting an audio recording according to embodiments.

According to an operation 1220, the patient input may be received, for example by the one or more processors. The patient input may include values for the ECG signal 1121.

According to another, optional operation 1230, it may be determined whether or not a deliberately generated trigger input was detected. The trigger input could have been generated by the patient 82 actuating the user trigger module 1145. If yes, then according to another operation 1240, at least some of the values of the ECG signal may start to be caused to be recorded in the memory. Optionally, if a microphone is provided, then according to one more operation 1250, audio data may also start to be caused to be recorded in the memory, responsive to the trigger input being detected and responsive to the received audio signal.

After the operation 1250, or if the answer to the operation 1220 is no, then according to another operation 1280, it can be determined from the patient input whether or not a shock criterion is met. If no, execution may return to the operation 1220, or to another operation to determine whether any started recording is to be stopped, as described further below.

If the answer to the operation 1280 is yes then, according to another operation 1290, at least some of the stored electrical charge can be caused to be discharged via a therapy electrode through the ambulatory patient 82, while the support structure is worn by the ambulatory patient 82, so as to deliver a shock to the ambulatory patient 82. After that, execution may return to the operation 1220.

It will be appreciated that the above can start one or more recordings. In such embodiments, the one or more processors can be further programmed to stop the recording in the memory, responsive to a stop ECG recording event occurring. The stop ECG recording event may be implemented in a number of ways. For instance, the stop ECG recording event can be the passage of a predetermined amount of time from when the deliberately generated trigger input was detected. Or, it can be the detection of another deliberately generated trigger input, of the same or different type than the trigger input 1170, such as a suitable voice command, as will be understood from the below. Or, it can be the passage of a predetermined amount of time from when a recording condition ends, such as an ECG episode ending, the cancel switch being released, or other variable changes. It will be observed that the different possible stop ECG recording events could result in recordings of different durations. An example is now described.

FIG. 13 shows a timing diagram 1300. A time axis 1308 shows sample time moments 1340, 1342, 1343, 1345, 1346. A block 1365 represents ambient sounds at various times, at least from the time moment 1340 to the time moment 1346.

A group 1370 shows deliberate recording trigger inputs that are detected by the processor. The group 1370 includes a trigger input 1371, detected at the time moment 1342, and a trigger input 1372, detected at the time moment 1345.

A group 1320 shows ECG recordings that are made as a result of the recording trigger inputs of the group 1370. The group 1320 includes a recording 1321, which starts at the time moment 1342 and ends at the time moment 1343. Therefore, the recording 1321 captures a portion 1361A of the ambient sounds 1365. The group 1320 also includes a recording 1322, which starts at the time moment 1345 and ends at the time moment 1346. Therefore, the recording 1322 captures a portion 1362A of the ambient sounds 1365. It will be observed that the recording 1322 is longer, in this example, than the recording 1321.

For embodiments where a microphone is also included, and the trigger input that starts the ECG recording is the same as the trigger input that starts the audio recording, a group 1390 shows sound recordings that are made as a result of the recording trigger inputs of the group 1370. The group 1390 includes a recording 1391, which starts at the time moment 1342 and ends at the time moment 1343. Therefore, the recording 1391 captures a portion 1361A of the ambient sounds 1365. The group 1390 also includes a recording 1392, which starts at the time moment 1345 and ends at the time moment 1346. Therefore, the recording 1392 captures a portion 1362A of the ambient sounds 1365. It will be observed that the recording 1392 is longer, in this example, than the recording 1391. So, for the time durations of 1361A, 1362A, concurrent ECG and audio data are available to a clinician for review.

Figure 11:
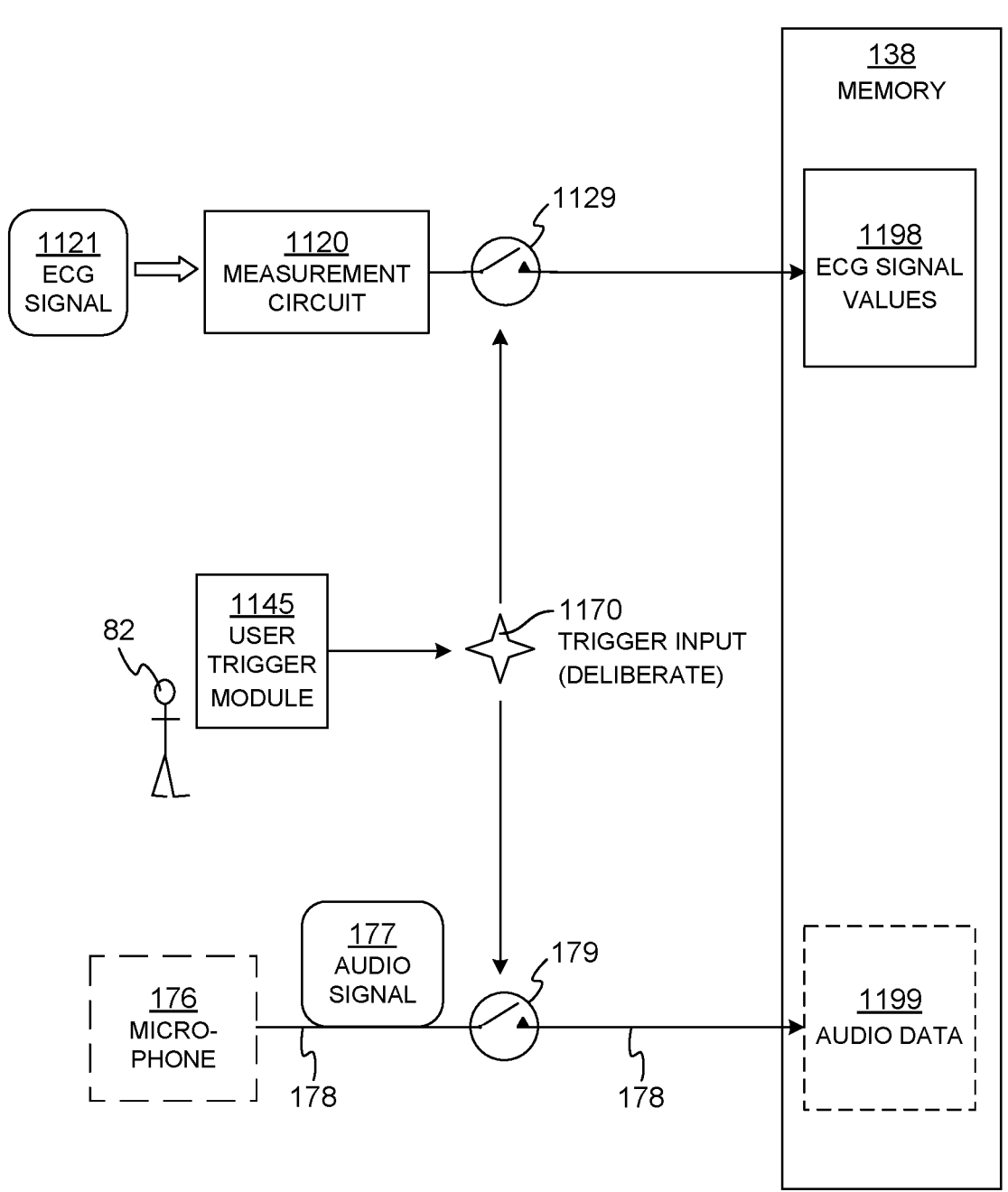
FIG. 11 is a diagram showing sample components where a user trigger module is used to start recording ECG data, and optionally also audio data, in a memory according to embodiments.

The user trigger modules 845 of FIG. 8 and 1145 of FIG. 11 are now described in more detail. Such user trigger modules 845, 1145 may be implemented in hardware, software, or a combination of both. In some embodiments, the user trigger module 845 can be a user input device of the UI 580. Additional embodiments are now described.

In some embodiments, the user trigger module is a voice recognition module that is designed to a) receive the audio signal, b) recognize, within the audio signal, a preset voice prompt, and c) generate the trigger input responsive to thus recognizing the preset voice prompt. In such embodiments, while the audio signal will start being recorded in response to the voice prompt, the recording may routinely start after the voice prompt, and not be captured in the audio data. The voice recognition module can be implemented in software, hardware, firmware, and so on. Examples are now described.

Figure 14:
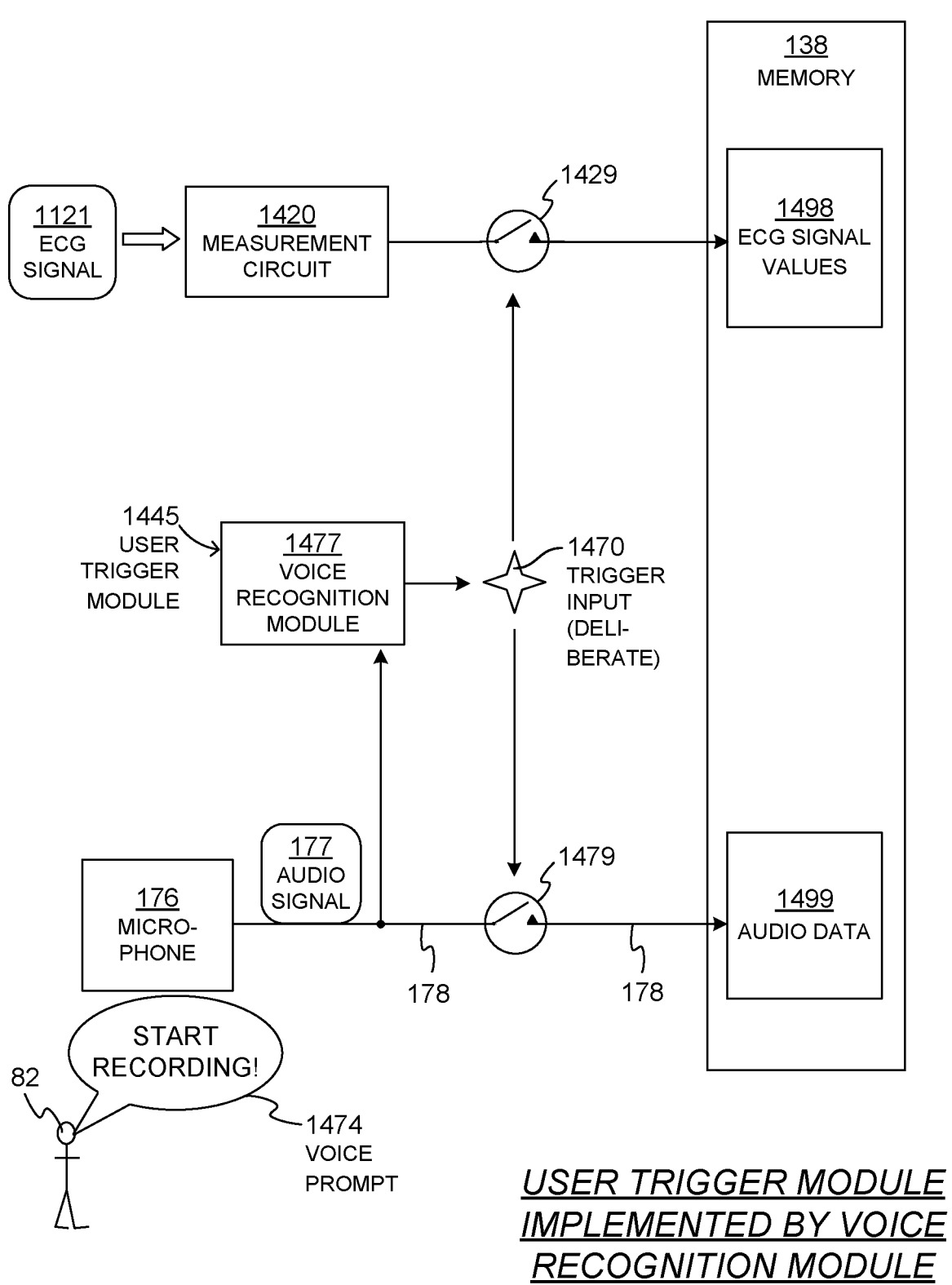
FIG. 14 is a diagram showing sample WMS components in embodiments where a user trigger module of FIG. 8

FIG. 14 has some similarities with FIG. 11. FIG. 14 shows again the memory 138, the microphone 176, the audio signal 177, and the arrow 178 of FIG. 1, and also of FIG. 8. The arrow 178 is interrupted by a switch 1479. The switch 1479 can be made as described for the switch 179.

In this example, the patient 82 has been trained to start the recording, and then give a preset, specific voice prompt 1474, within the vicinity of the microphone 176. The voice prompt can be words such as: "hear me" or "start recording". When spoken by the patient 82, the voice prompt 1474 is therefore captured within the audio signal 177, along with the ambient sounds.

A voice recognition module 1477 implements a user trigger module 1445. In particular, the voice recognition module 1477 is designed to a) receive the audio signal 177, and b) recognize, within the audio signal 177, the preset voice prompt 1474 among the ambient sounds. The recognition can be also with prior training of the voice recognition module 1477 to the voice of the patient 82, perhaps uttered under various simulated states of calm, stress, and so on. The voice recognition module 1477 can be further designed to generate a trigger input 1470 responsive to thus recognizing the preset voice prompt 1474. And, the switch 1479 can close responsive to the trigger input 1470, which then causes audio data 1499 to be recorded in the memory 138 responsive to the audio signal 177.

In additional embodiments, the voice recognition module 1477 can be further trained to recognize a condition of the patient from elements of the voice, and to capture that as well. For instance, the voice recognition module 1477 may recognize that the patient 82 is about to have an SCA.

ECG recording can be caused to be initiated by the same trigger input 1470. In particular, FIG. 14 further shows a measurement circuit 1420 that can be as the measurement circuit 520, and which receives the ECG signal 1121. The trigger input 1470 can close a switch 1429, which enables starting to cause at least some of the values 1498 of the ECG signal 1121 to be recorded in the memory 138. The switch 1429 can be made as described for the switch 1129.

Figure 15:
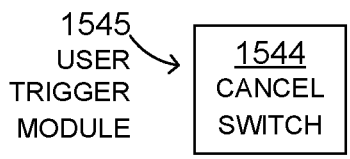
FIG. 15 is a diagram showing a sample WMS component in embodiments where a user trigger module of FIG. 8

In some embodiments, the user trigger module of FIG. 8 or FIG. 11 is implemented by the cancel switch of the WMS system. For instance, FIG. 15 shows a cancel switch 1544. The cancel switch 1544 also implements a user trigger module 1545, with appropriate design, programming and so on. Equivalently, the user trigger module 1545 operates as the cancel switch 1544. In such embodiments, the stored electrical charge is not caused to be discharged responsive to detecting the generated trigger input, even though the shock criterion is met. Such embodiments include the output device that is configured to output a human-perceptible warning prompt, and the one or more processors are further programmed to: cause, responsive to the shock criterion being met, the output device to output a Human Perceptible Indication (HPI), then wait for a preset amount of time, and then cause, responsive to the deliberately generated trigger input not being detected during the preset amount of time, at least some of the stored electrical charge to be thus discharged so as to deliver a shock to the ambulatory patient, but, if the deliberately generated trigger input is detected during the preset amount of time, not cause any of the stored electrical charge to be thus discharged responsive to the shock criterion being met.

In some embodiments, the user trigger module of FIG. 8 or FIG. 11 is implemented in a peripheral device of the WMS system. In particular, in such embodiments, the energy storage module can be provided within the unit, for instance as shown in FIG. 5 for the energy storage module 550 being provided within the unit 500. In addition, a peripheral device that is distinct from the unit, is configured to be in electronic communication with the unit, and includes the user trigger module. Such a peripheral device can be a custom-made device that is part of the WMS. Or, such a peripheral device can be a wireless telephone, a smartphone, a Personal Digital Assistant (PDA), a personal electronic device, a pager, a laptop computer, a tablet, an e-reader, and so on. It can store and run a software application, also known as app, made according to embodiments, so as to perform various functions as described. Examples are now described.

Figure 16:
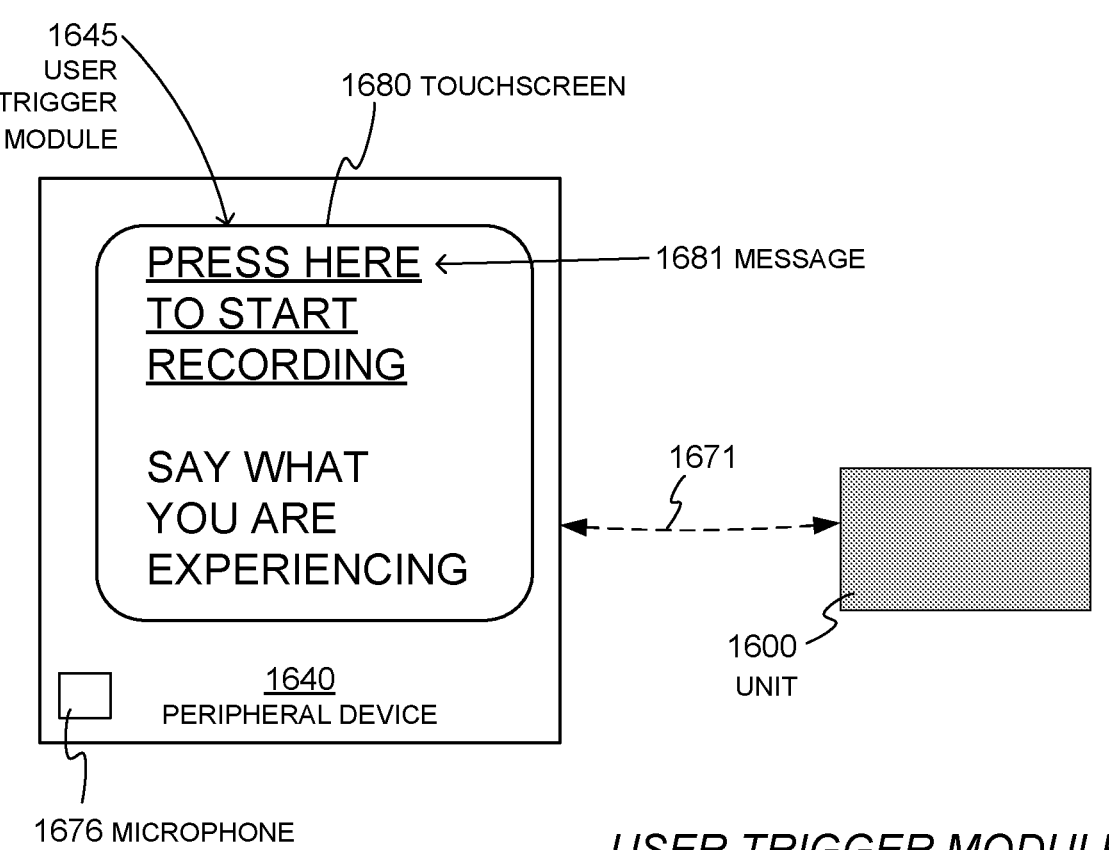
FIG. 16 is a diagram showing sample WMS components in embodiments where a user trigger module of FIG. 8

Referring to FIG. 16, in embodiments the WMS has a unit 1600, which can be as described above for the units 100 or 500. In addition, the patient 82 carries a peripheral device 1640 on their person for typically much of the day. The peripheral device 1640 can be part of the WMS or not, as per the above. The patient 82 may carry the device 1640 in a pocket, in a special holder, or even wear it on their wrist. The patient 82 may use the device 1640 to communicate with parts of the WCD system, for example via a communications line 1671, wireless or wired, with the unit 1600.

In some embodiments, the user trigger module includes a touchscreen on the peripheral device. For instance, the peripheral device 1640 has a touchscreen 1680 that implements a user trigger module 1645. In particular, the touchscreen 1680 can project the shown message 1681. The message 1681 can also be a hyperlink which, when touched, generates the above-described trigger input.

In some embodiments, the peripheral device includes the microphone. For instance, the peripheral device 1640 also includes a microphone 1676, which may perform some of the above-described functions.

In some of these embodiments, the above-described voice recognition takes place on the peripheral device. For instance, the user trigger module can instead be a voice recognition module within the peripheral device, and which is designed to: receive the audio signal, recognize, within the audio signal, a preset voice prompt, and generate the trigger input responsive to thus recognizing the preset voice prompt.

Returning to FIG. 1, in embodiments, the memory 138 always records all the audio, no matter when it happens. In other embodiments, the memory 138 optionally includes a prior capture feature 139, in which it captures and retains audio recordings made before there was a trigger that caused it to start recording. In such embodiments, the WMS may continuously record audio and then discard it. The WMS may detect that a recording trigger was generated and, in response, stop the discarding, which amounts to starting a recording. This, however, additionally captures audio recorded before it was detected that a recording trigger was generated. Examples are now described.

Figure 17A:
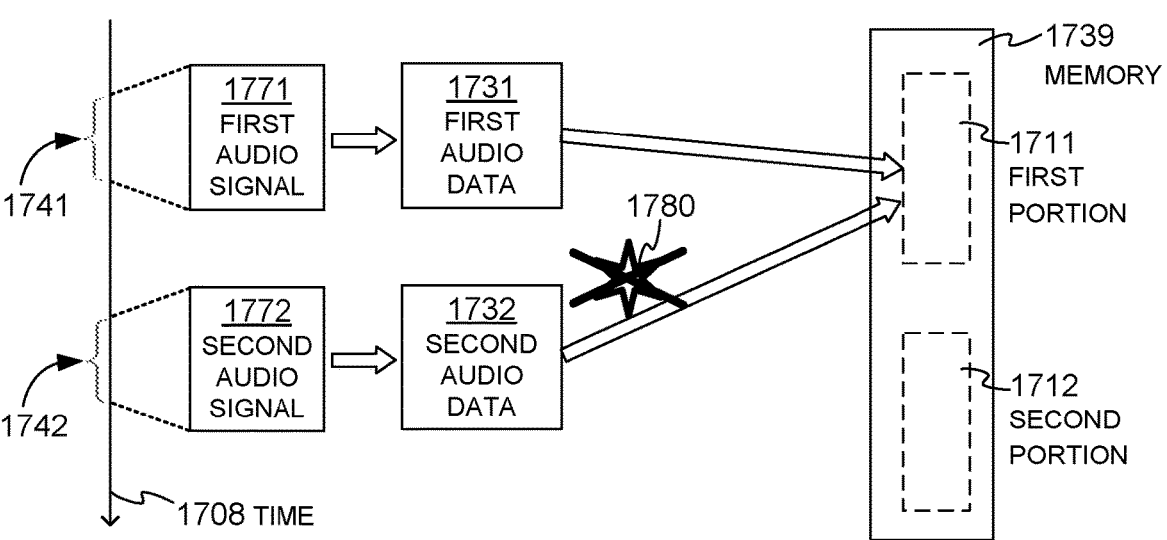
FIG. 17A is a diagram showing sample memory locations where audio data may be recorded if no recording trigger is detected, according to embodiments.
Figure 17B:
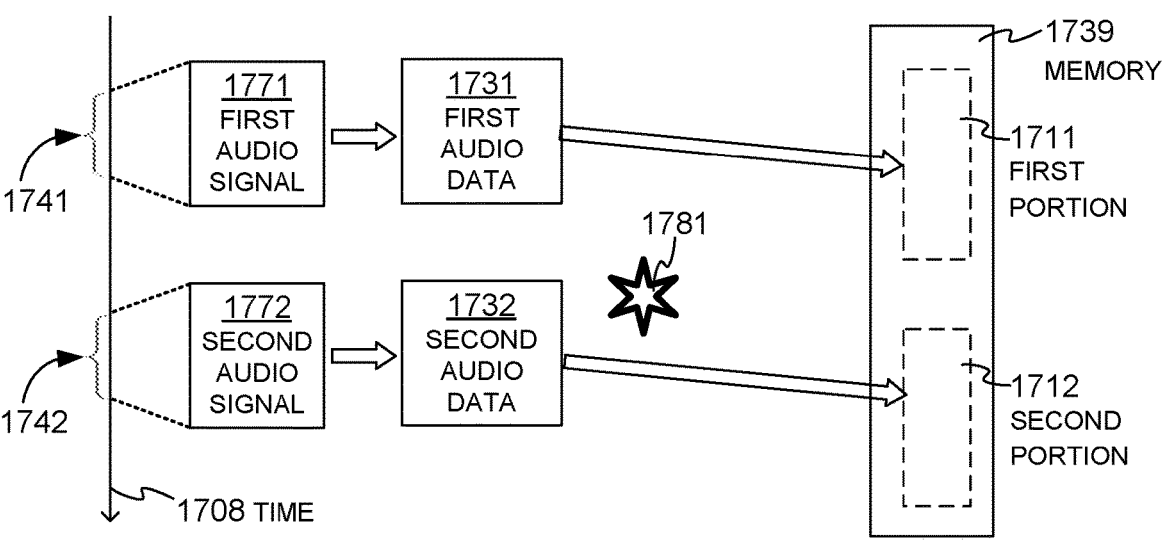
FIG. 17B is a diagram showing sample memory locations where audio data may be recorded if a recording trigger is indeed detected, according to embodiments.

FIGS. 17A and 17B have similarities and differences. In each of them, a memory 1739 can be as described for the memory 138, but it also includes the prior capture feature 139. The memory 1739 has a first portion 1711 and a second portion 1712. The second portion 1712 is different from the first portion 1711. These two portions are not shown adjacent each other, because that is not required. Of course, in embodiments, the second portion 1712 of the memory 1739 can be adjacent to the first portion 1711 of the memory 1739.

Moreover, in each of FIGS. 17A and 17B, the microphone (not shown), is configured to output, responsive to ambient sounds, a first audio signal 1771 and then a second audio signal 1772. A vertical time axis 1708 shows sample time durations 1741, 1742, during which these audio signals 1771, 1772 are output. In this example, the time durations 1741, 1742 do not follow immediately each other, because that is not required. Of course, in embodiments, the second audio signal 1772 could be output immediately after the first audio signal 1771.

The one or more processors can be programmed to generate a recording trigger, responsive to a recording condition being met. A recording trigger can be implemented in the same was a trigger input. A recording condition can be the same as a logical criterion, such as the shock criterion, and examples are described later.

The one or more processors can be further programmed to cause, responsive to the first audio signal 1771, first audio data 1731 to be recorded in the first portion 1711 of the memory 1739, as shown in both diagrams.

The one or more processors can be further programmed to detect whether or not a recording trigger was generated while thus causing the first audio data 1731 to be recorded. The answer may determine to which portion of the memory the second audio data 1732 will be recorded. In particular:

In the example of FIG. 17A, the recording condition is not met, and therefore a recoding trigger is not generated. This is depicted by drawing a recoding trigger 1780 and crossing it out.

The one or more processors can be further programmed to, responsive to detecting that a recording trigger 1780 was not generated while thus causing the first audio data 1731 to be recorded, cause, responsive to the second audio signal 1772, second audio data 1732 to be recorded in the first portion 1711 of the memory 1739, thus erasing the recorded first audio data 1731 from the first portion 1711 of the memory 1739. The erasing is caused because the second audio data 1732 is written or recorded over first audio data 1731, in the same first portion 1711 of the memory 1739.

FIG. 17B is for the situation where a recording trigger 1781 is generated while the first audio data 1731 is being recorded. For such an occasion, the one or more processors can be further programmed to, responsive to detecting that a recording trigger 1781 was generated while thus causing the first audio data 1731 to be recorded, cause, responsive to the second audio signal 1772, the second audio data 1732 to be recorded in the second portion 1712 instead of in the first portion 1711. As such, the earlier-recorded first audio data 1731 is not over-written, and thus preserved. That, even though this first audio data 1731 was recorded before it was signified, by the recording trigger 1781, that recording of audio should start.

Examples of the recording condition are now provided. In some embodiments, the recording condition is a physiological event of the patient, which is of interest. For instance, the recording condition can be the shock criterion, in which case the trigger input is received responsive to the shock criterion being met.

In some embodiments, the parameter of the ambulatory patient includes an Electrocardiogram (ECG) signal of the patient, the sensor includes sensing electrodes configured to sense the ECG signal, and the patient input includes values for the ECG signal. In such embodiments, the recording condition can be met responsive to the values for the ECG signal meeting a trigger criterion. A number of trigger criteria can be implemented. For instance, the trigger criterion is met responsive to the values for the ECG signal indicating a heart rate higher than a threshold, or a pulse width higher than a threshold, or a pulse width lower than a threshold.

In some embodiments, the recording trigger is generated by deliberate patient action, as per the above. For instance, a user trigger module may be provided, which can be configured to enable the patient to deliberately generate the recording trigger. In other words, the recording trigger can be generated by the patient deliberately actuating the user trigger module. The recording trigger can be of course as described above for the trigger input. In such cases, therefore, the user trigger module can be a voice recognition module that is designed to: receive the audio signal, recognize, within the audio signal, a preset voice prompt, and generate the recording trigger responsive to thus recognizing the preset voice prompt. In addition, the energy storage module can be provided within a unit, and a peripheral device that is distinct from the unit can be configured to be carried by the ambulatory patient, to be in electronic communication with the unit, and includes the user trigger module.

Figure 18:
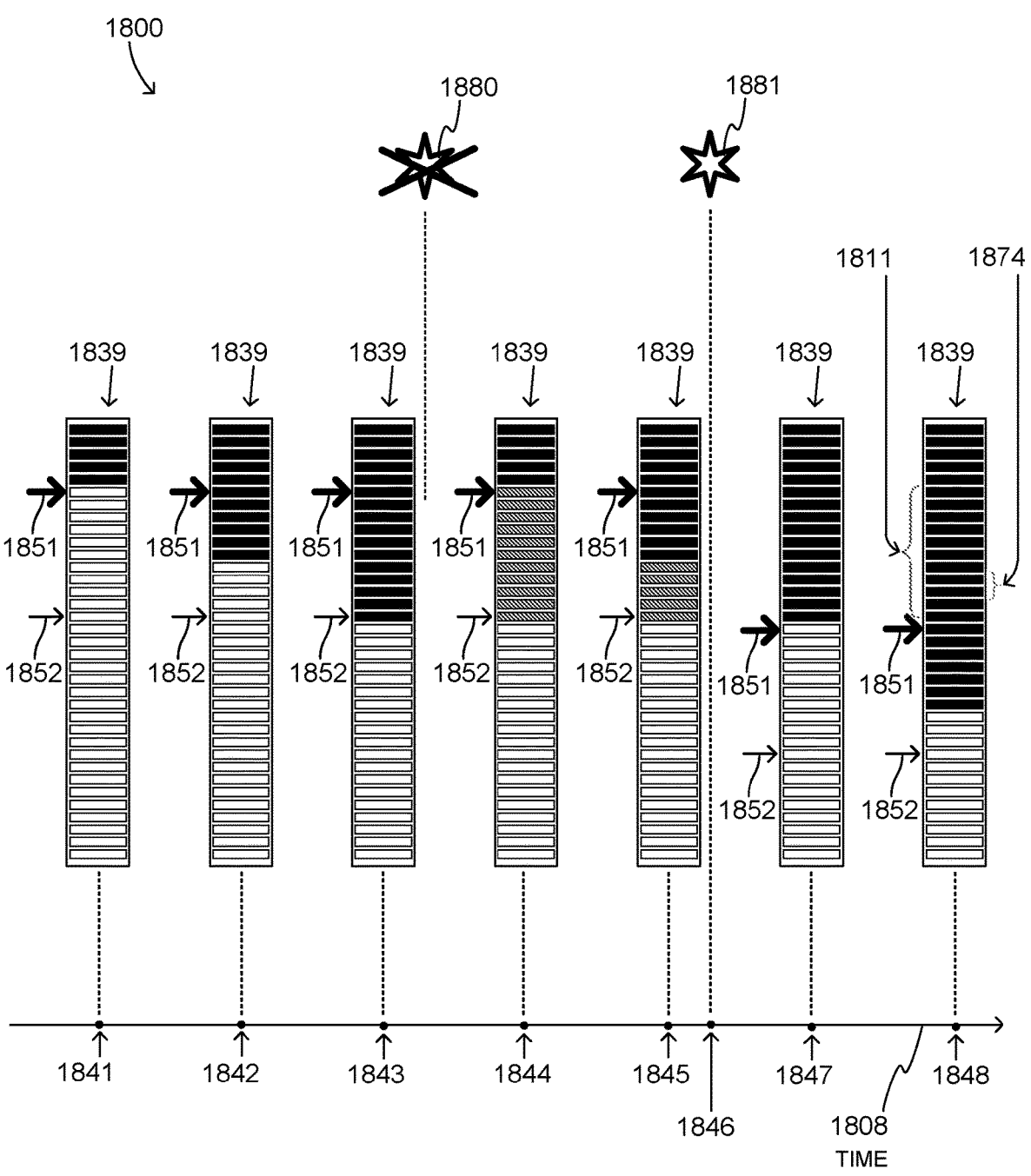
FIG. 18 shows successive diagrams of a sample memory storing audio data depending on whether or not there was a recording trigger, according to embodiments.

FIG. 18 shows the states of a memory 1839 at different time moments 1841, 1842, 1843, 1844, 1845, 1847, 1848 of a time axis 1808. In each instance, the memory 1839 stores audio data in registers, which are shown as vertically stacked horizontal blocks. A block that contains audio recording is shown as filled, while one that does not, i.e. is "empty", is shown only as an outline. A group of successive such blocks could be one of the memory portions 1711, 1712 in FIGS. 17A, 17B. As will be appreciated from the below, in the example of FIG. 18, the second portion of the memory is adjacent to the first portion of the memory, and the second audio signal is output immediately after the first audio signal.

In the example of FIG. 18, between the time moments 1843 and 1844, it is detected that a recording trigger has not been generated during a certain time, namely between the time moments 1841 and 1843. This is shown by a recording trigger 1880 that is crossed out—this is a special case of FIG. 17A. And, by the time moment 1846, it is detected that a recording trigger 1881 has been generated during the updated certain time between the time moments 1844 and 1847— this is a special case of FIG. 17B.

In some embodiments, the one or more processors are further programmed to set a begin pointer to point to the first portion of the memory. In the example of FIG. 18, at the time moment 1841, a begin pointer 1851 is set to point to the first register of a first portion of the memory 1839. In addition, an end pointer 1852 is set to point to the last register of the first portion. As such, the first portion of the memory is the group of registers pointed to, at the time moment 1841, between the begin pointer 1851 and the end pointer 1852.

The end pointer 1852 can be automatically set with reference to the begin pointer 1851, for instance to include a fixed number of registers. This defines the size of the first portion of the memory. The size could be set to contain, say, two minutes of audio recording, or five minutes, and so on. If the number of registers is fixed every time, then the second memory portion will have the same size as the first, and so on.

In embodiments such as the example of FIG. 18, the first audio data is recorded in the first portion of the memory responsive to the begin pointer pointing to the first portion of the memory. In particular, the incoming first audio data is pointed to be stored in the registers starting from where the begin pointer 1851 points to. By the time moment 1842, the first audio data is being recorded in more registers of the first portion—in particular filling in the first register that is pointed to by the begin pointer 1851 and then some subsequent registers. The registers of the first portion that have been recorded/written in are shown filled in black. And, at the time moment 1843, the first audio data finishes being recorded in the first portion, filling in the last register that is pointed to by the end pointer 1852.

As mentioned above, between the time moments 1843 and 1844 it is detected that a recording trigger has not been generated. As such, at the time moment 1844, the begin pointer 1851 has not moved. Accordingly, the end pointer 1852 has not moved either, and they both point to the same set of registers. In such embodiments, the second audio data, which comes after the first audio data, is recorded in the first portion of the memory responsive to the begin pointer 1851 pointing to the first portion of the memory. As such, the first portion will be over-written, which is indicated by the registers of the first portion now being filled in grey; they do store audio data, but that data will be over-written and lost. In particular, the incoming second audio data is pointed to be stored in the registers starting from where the begin pointer 1851 points to. By the time moment 1845, the second audio data is being recorded in the first portion, filling in the first register that is pointed to by the begin pointer 1851 and then some subsequent registers.

The scenario so far will be repeated over and over, continuing to record only in the first portion of the memory 1839 for as long as no generated recording trigger is being detected by the one or more processors. This does not waste much of the memory 1839, with recordings that will not be kept.

Now embodiments are described where a generated recording trigger 1881 is detected by the one or more processors at the time moment 1846. For that description, in order to use again FIG. 18, the audio data shown recorded between the time moments 1845, 1847, is now considered the first audio data. In such embodiments, responsive to thus detecting that a recording trigger was generated, the one or more processors are further programmed to set the begin pointer to point instead to the second portion of the memory. In the example of FIG. 18, at the next time moment 1847, the begin pointer 1851 is set to point instead to the first register of a second portion of the memory 1839. This is the register after the one that was previously pointed to by the end pointer 1852. In addition, the end pointer 1852 is set to point instead to the last register of the second portion. In such embodiments, then, the second audio data is recorded in the second portion of the memory responsive to the begin pointer 1851 pointing to the second portion of the memory 1839. An instant of such recording is seen at the time moment 1848.

In the memory 1839, at the time moment 1848, the first portion includes a first group of registers 1811. The begin pointer 1851 was set to point to the first portion of the memory by pointing to one of the first group of registers. The second portion of the memory includes a second group of the registers, namely those pointed to by the begin pointer 1851 and the end pointer 1852. The begin pointer 1851 is set to point to the second portion of the memory by pointing to one of the second group of registers.

As seen at the time moment 1848, the memory 1839, will retain the first audio data in the group 1811. In this example, a voice prompt was used to start the recording such as the voice prompt 1474 of FIG. 14. In FIG. 18, a group 1874 of memory registers also stores audio data from the voice prompt 1474. As such, the voice prompt itself will be retained as audio data, even though it was spoken before it caused the recording trigger 1881 to be generated.

It will be appreciated that the above can start retaining an already-made recording, instead of over-writing it and thus erasing what was there before. In such embodiments, the one or more processors can be further programmed to resume discarding the already-made recordings, for instance using techniques such are described above for stop audio recording events and for stop ECG recording events. Examples of recordings are now described.

Figure 19:
FIG. 19 is a timing diagram showing durations of recordings resulting from recording triggers, according to embodiments.

FIG. 19 shows a timing diagram 1900. A time axis 1908 shows sample time moments 1940, 1941, 1942, 1943, 1944, 1945, 1946. A block 1965 represents ambient sounds at various times, at least from the time moment 1940 to the time moment 1946.

A group 1980 shows recording triggers that are detected by the processor. The group 1980 includes a recording trigger 1981, detected at the time moment 1942, and a recording trigger 1982, detected at the time moment 1945. Note, as per the above, these can be generated either due to a physiological event of the patient and/or due to a deliberate patient action.

A group 1990 shows sound recordings that are made as a result of the recording trigger inputs of the group 1980. The group 1990 includes a recording 1991, which starts at the time moment 1941 and ends at the time moment 1943.

Therefore, the recording 1991 captures portions 1961P and 1961A of the ambient sounds 1965. The group 1990 also includes a recording 1992, which starts at the time moment 1944 and ends at the time moment 1946. Therefore, the recording 1992 captures portions 1962P and 1962A of the ambient sounds 1965.

It will be observed that the portions 1961P and 1962P of the ambient sounds 1965 occur before their respective recording triggers 1981, 1982, as was demonstrated in FIG. 18. In fact, these may include recordings of voice prompts 1974. Indeed, the time instances 1942, 1945 is when the recording triggers 1981, 1982 are detected by the system, but the action to generate them (1974) may have taken place before that.

Figure 20:
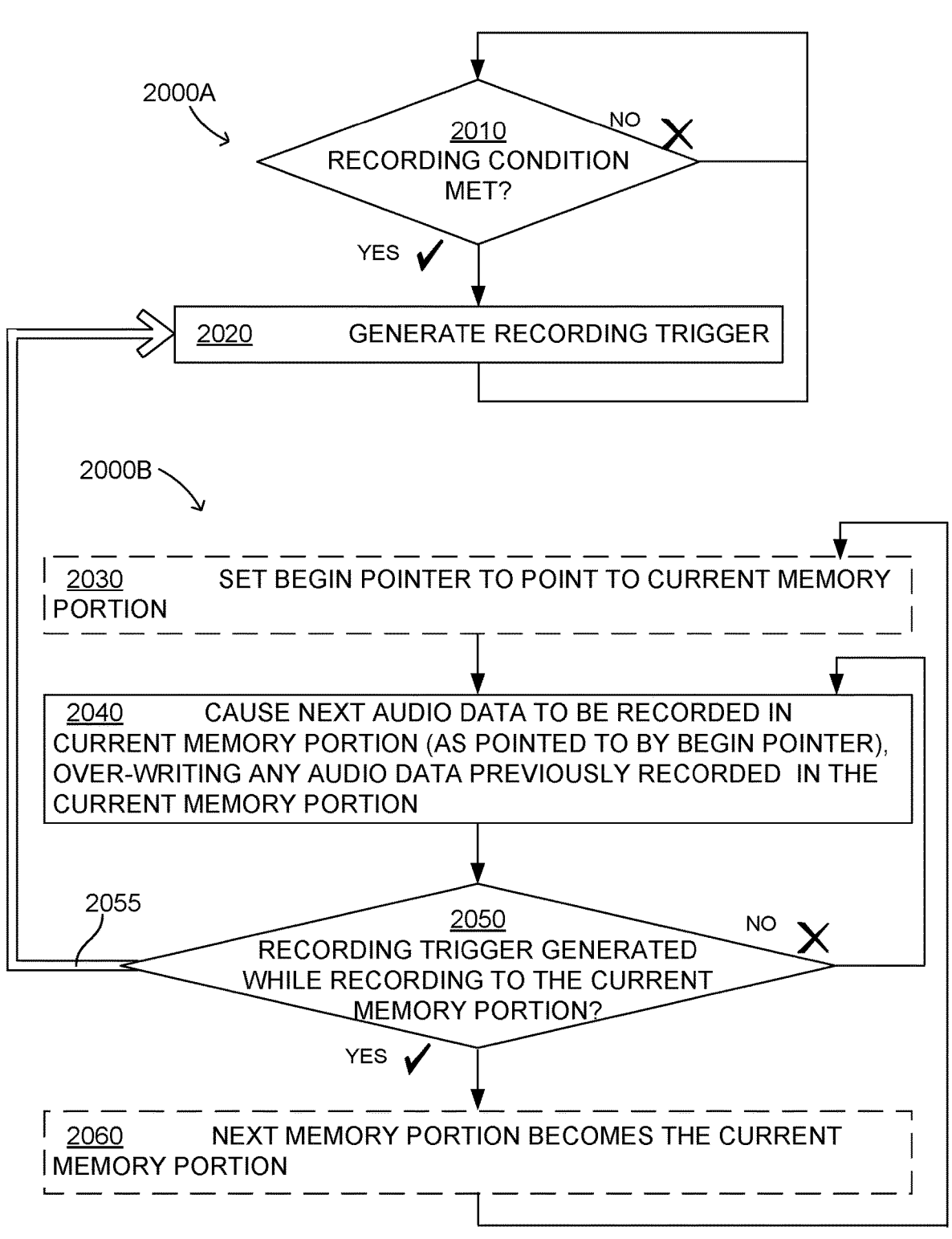
FIG. 20 shows a set of two related flowcharts for illustrating sample methods according to embodiments.

FIG. 20 shows two related flowcharts 2000A, 2000B for describing methods according to embodiments. Each of these flowcharts can be iterated multiple times. These two flowcharts 2000A, 2000B may operate independently of each other but, at some point, one of them looks up something of the other, as described below.

In the flowchart 2000A, according to an operation 2010, it is determined whether or not a recording condition is met. If no, then execution may return to the operation 2010. If yes then, according to another operation 2020, a recording trigger is generated responsive to the recording condition being met. Then execution may return to the operation 2010.

Using the flowchart 2000B, two sample iterations are considered and described. In the first considered iteration, a current portion of the memory is the first portion.

According to an optional operation 2030, a begin pointer can be set to point to the current portion of the memory. This operation is performed only if a begin pointer is used.

According to another operation 2040, next audio data can be caused to be recorded in the current portion of the memory. In the first iteration, the current portion of the memory is the first portion, and the next audio data will be first audio data, which can be caused to be recorded responsive to a first audio signal.

The recording of the operation 2040 can be performed as pointed to by the begin pointer, if the operation 2030 has taken place. Moreover, the recording of the operation 2040 can be performed while over-writing, and thus erasing, any audio data previously recorded in the current memory portion.

According to another operation 2050, it can be detected whether or not a recording trigger was generated, while thus causing the audio data to be recorded during the operation 2040. A recording trigger may have been generated at the operation 2020 of the other flowchart 2000A, as shown by a lookup arrow 2055. That lookup arrow 2055, however, does not indicate that execution transfers the other flowchart 2000A. If no, then execution returns to the operation 2040; and if a begin pointer is used, it need not be reset.

If at the operation 2050 the answer is yes then, according to another, optional operation 2060, the next memory portion becomes the current memory portion. This can be accomplished by internal settings, or implemented only notionally and not as a separate operation. This would start the second iteration, execution may return to the operation 2030, and the begin pointer is set to another memory portion accordingly. In the second iteration, at the operation 2040 there is no over-writing of the immediately previously recorded audio data, and so on.

Returning to FIG. 1, in some embodiments, the shown memory 138 is in the unit 100, as indicated by bent lines to the unit 100. In such embodiments, one or more processors are also in the unit 100. In addition, these one or more processors are programmed to cause audio data to be recorded in the memory 138 responsive to the audio signal 177. In capturing the audio signal and causing the audio data to be thus recorded, any one of the improvements described above may be used, alone or in combination with others.

In addition, these one or more processors can be further programmed to create a standalone computer file 141 that has audio-related data 164, which is generated from the recorded audio data. Moreover, these one or more processors are further programmed to store the standalone computer file 141 in the memory 138, such that the computer file 141 can be accessed by a general-purpose computer 125. The general-purpose computer can be controlled by an other processor 127 that is not in the unit 100 and is not one of the one or more processors in the unit 100. The general-purpose computer can be a portable device that a responding Emergency Medical Technician can access straight from the unit 100, or from an associated peripheral, with a local connection. Of course, the WMS may include access controls to protect the captured audio from improper access. For example, EMTs can be given a password or a security fob to access the unit or a peripheral device. Or, the general-purpose computer can be in a remote location that has an attendant who can be notified of the patient-triggered event and can access the captured audio. For example, an attendant can notify a 911 Computer-Aided Dispatch (CAD) system and forward the captured audio, which the CAD system in turn can forward to the responding Emergency Medical Technician.

The accessibility of the standalone computer file 141 or, equivalently, a copy of it by the general-purpose computer 125 may be implemented in a number of ways. In some embodiments, the one or more processors are further programmed to simply transmit the computer file 141 to the general-purpose computer 125. In some embodiments, the general-purpose computer 125 has a computer interface, and the computer file 141 can be accessed by the general-purpose computer 125 by being exported to the general-purpose computer via the computer interface. The export can be controlled either by the general-purpose computer 125 or by the unit 100. For such embodiments, the computer interface can be a USB port or equivalent, or a wireless connection, and the unit 100 may have a compatible connection. In some embodiments, the general-purpose computer 125 is a personal electronic device of the WMS that is configured for use by the patient. The clinician may review the file 141 from there. In some embodiments, the WMS further includes a peripheral device configured for use by the patient. In such embodiments, the computer file is exportable first to the peripheral device, and from the peripheral device to the general-purpose computer 125. In such embodiments, further signaling and coordination may be further performed between the peripheral device and the unit 100 for the association. For instance, they may coordinate their clocks, the naming of the computer file 141 recognizing that there may be multiple such computer files, the exporting, and so on, so that the clinician will coordinate the audio data with the concurrent physiological data.

In some embodiments, the audio-related data is sound data that is designed to be playable by a sound player application of the general-purpose computer 125. An example is now described.

Figure 21:
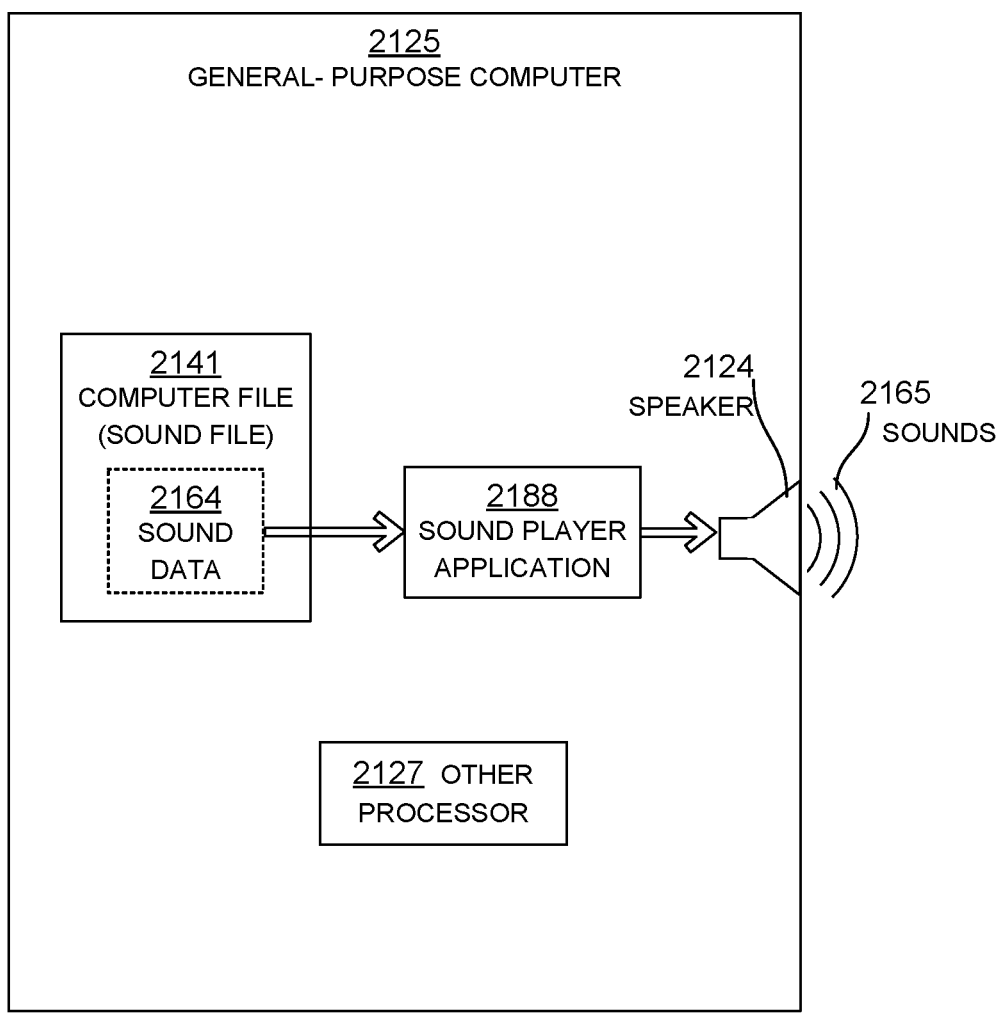
FIG. 21 is a diagram showing a sample implementation of recorded audio-related data in a computer file that is a sound file, according to embodiments.

FIG. 21 shows a general-purpose computer 2125, which can be as described for the general-purpose computer 125. The general-purpose computer 2125 is controlled by an other processor 2127, which can be as described for the other processor 127. The general-purpose computer 2125 has a speaker 2124, and a sound player application 2188. A computer file 2141 has been created by the WMS as described with reference to FIG. 1, and is now stored in a memory of the general-purpose computer 2125. The computer file 2141 can be, in such embodiments, a sound file. The computer file 2141 has sound data 2164, which are an embodiment of the audio-related data 164. When the sound data 2164 is played by the sound player application 2188 to the speaker 2124, it causes sounds 2165 to be played for the reviewing clinician. Ideally, the sounds 2165 reproduce the ambient sounds 165.

In some embodiments, the one or more processors are further programmed to recognize a voice in the audio signal, which is often the voice of the patient. In such embodiments, the one or more processors are further programmed to create a text transcription of the recognized voice, and the computer file includes the text transcription. The text transcription can be created by a voice recognition module, and so on. Examples are now described.

Figure 22:
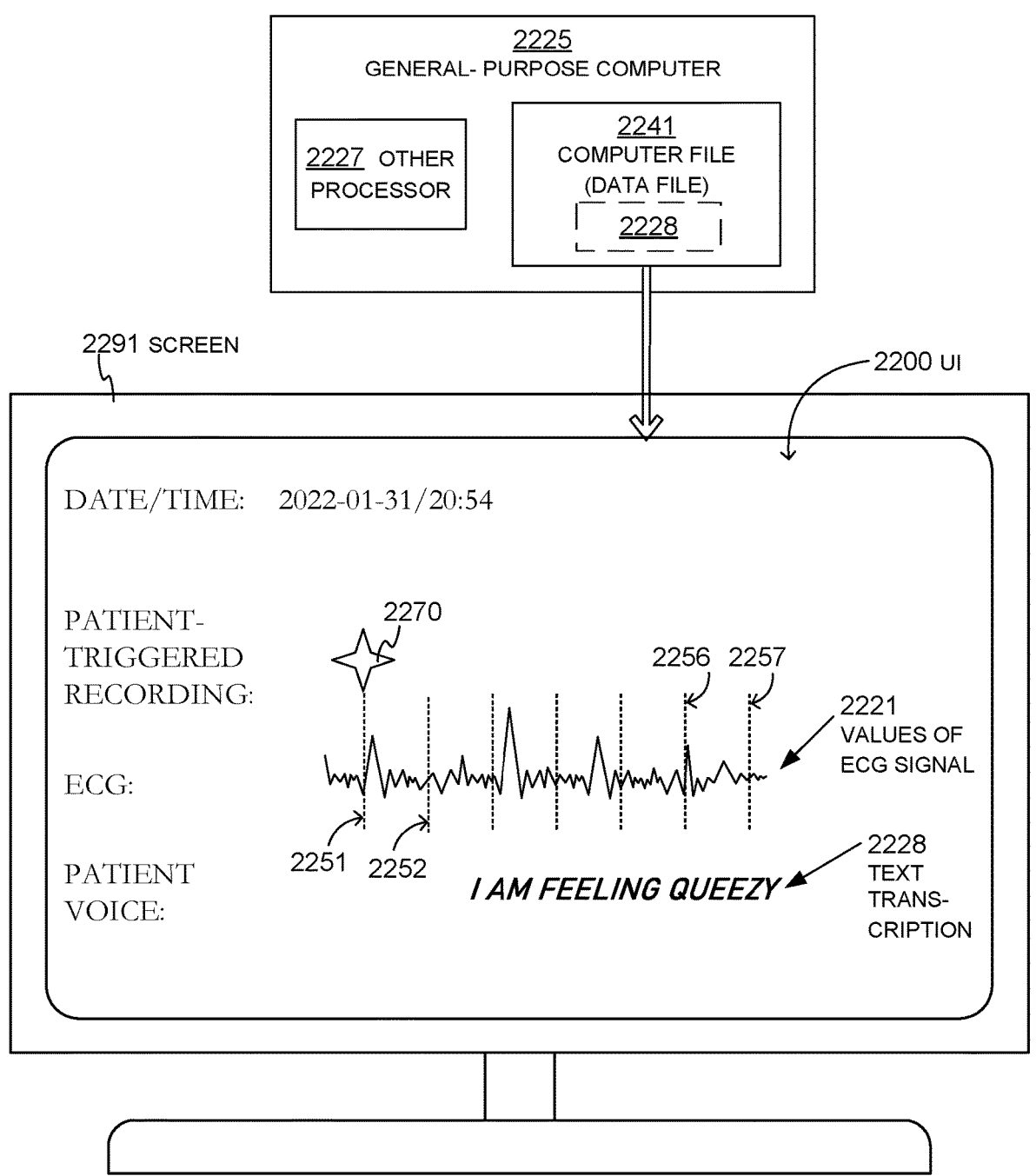
FIG. 22 is a diagram showing a sample implementation of recorded audio-related data whose voice has been detected and converted into a voice transcription, according to embodiments.

FIG. 22 shows a general-purpose computer 2225, which can be as described for the general-purpose computer 125. The general-purpose computer 2225 is controlled by an other processor 2227, which can be as described for the other processor 127. A computer file 2241 has been created by the WMS as described with reference to FIG. 1, and is now stored in a memory of the general-purpose computer 2225. The computer file 2241 includes a text transcription 2228.

A clinician might view the computer file 2241 by using a computer screen 2291 that is connected to the general-purpose computer 2225. The computer screen 2291 may project a user interface (UI) 2200, which shows the contents of the computer file 2241.

At the top of the UI 2200, the clinician may view the date and time of events. At the top of the UI 2200, the clinician may view the text transcription 2228.

In some embodiments, the parameter includes an Electrocardiogram (ECG) signal of the patient, the sensor includes sensing electrodes configured to sense the ECG signal, the patient input includes values for the ECG signal, and the computer file includes the values for the ECG signal and includes the text transcription in time-relation with the values for the ECG signal. Files that include the ECG signal are sometimes called episode files, especially when there was an episode in the ECG signal. In such embodiments, the clinician may also view the values for the ECG signal 2221 at that time. In fact, the text transcription 2228 can be included in time-relation with the values for the ECG signal 2221. The time-relation is communicated with short vertical time lines, of which only are view are labeled 2251, 2252, 2256, 2257. In such embodiments, the speed of speech is not the same as the horizontal time axis of the ECG values 2221, and the time-relation can be only for the beginning of the speech.

In some embodiments, the computer file 2241 also includes an indication of when the patient deliberately generated a trigger input. In such embodiments, the indication can be visible in the UI 2200. For instance, an indication 2270 is shown. The patient obviously initiated this, and then spoke, and the speech was transcribed as: "I AM FEELING QUEEZY" (2228).

FIG. 23 shows a flowchart 2300 for describing methods according to embodiments.

According to an operation 2320, the patient input may be received, for example by the one or more processors.

According to another operation 2340, audio data may be caused to be recorded in a memory, responsive to an audio signal.

According to another operation 2350, a standalone computer file can be created that has audio-related data which is generated from the recorded audio data.

According to another operation 2370, the standalone computer file can be stored in a memory, such that the computer file can be accessed by a general-purpose computer. The general-purpose computer can be as described above.

According to another operation 2380, it can be determined from the patient input whether or not a shock criterion is met. If no, execution may return to the operation 2320, or to another operation.

If the answer to the operation 2380 is yes then, according to another operation 2390, at least some of the stored electrical charge can be caused to be discharged via a therapy electrode through the ambulatory patient 82, while the support structure is worn by the ambulatory patient 82, so as to deliver a shock to the ambulatory patient 82. After that, execution may return to the operation 2320.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

At least one of the methods of this description, when implemented by a computer, can be performed differently at the rate of at least 10 times per second.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet (ADS) of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable medical system (WMS) for an ambulatory patient, comprising:
    a support structure configured to be worn by the ambulatory patient;
    a sensor configured to sense one or more parameters of the ambulatory patient;
    a measurement circuit configured to render a patient input responsive to the sensed one or more parameters;
    an energy storage module configured to store an electrical charge;
    a therapy electrode coupled to the energy storage module and configured to be maintained on a body of the ambulatory patient when the support structure is worn by the ambulatory patient;
    a microphone configured to output an audio signal responsive to ambient sounds, wherein the microphone is further configured to continuously record and discard audio data corresponding to the audio signal;
    a memory;
    a user trigger module configured to enable the ambulatory patient to generate a trigger input; and
    one or more processors programmed to:
        receive the patient input responsive to the sensed one or more parameters,
        determine, based on the received patient input, whether a shock criterion is met, wherein the shock criterion is met when the one or more parameters cross a threshold value,
        issue, responsive to the shock criterion being met, a prompt for a preset amount of time indicating the ambulatory patient to generate the trigger input within the preset amount of time,
        detect the generated trigger input,
        cause, responsive to the detected trigger input, the audio data to be recorded in the memory, wherein causing the audio data to be recorded stops the discarding of the audio data, wherein the audio data is recorded for a predetermined time interval, and wherein the memory is configured to retain audio recordings made prior to the detected trigger input; and
        create an exportable computer file comprising the recorded audio data for clinical review.

2. The WMS of claim 1, in which:
    the parameter includes an Electrocardiogram (ECG) signal of the patient,
    the sensor includes sensing electrodes configured to sense the ECG signal,
    and the patient input includes values for the ECG signal.

3. The WMS of claim 1, wherein:
    the one or more processors are further programmed to:

stop the audio data recording in the memory, responsive to a stop audio recording event occurring, wherein the stop audio recording event occurs after the trigger input is generated.

4. The WMS of claim 3, in which:
    the stop audio recording event is passage of a predetermined amount of time from when the generated trigger input was detected.

5. The WMS of claim 3, in which:
    the stop audio recording event is the detection of another generated trigger input.

6. The WMS of claim 1, in which:
    the user trigger module is a voice recognition module that is designed to:
        receive the audio signal,
        recognize, within the audio signal, a preset voice prompt, and
        generate the trigger input responsive to thus recognizing the preset voice prompt.

7. The WMS of claim 1, further comprising:
    an output device configured to output a human-perceptible warning prompt, wherein:
    the one or more processors are further programmed to:
        cause, responsive to the shock criterion being met, the output device to output a Human Perceptible Indication (HPI),
        wait for the preset amount of time after the HPI is output, and
        cause, responsive to the generated trigger input not being detected during the preset amount of time, at least some of the stored electrical charge to be thus discharged so as to deliver a shock to the ambulatory patient, and
        responsive to the generated trigger input being detected during the preset amount of time, not cause any of the stored electrical charge to be thus discharged responsive to the shock criterion being met.

8. The WMS of claim 1, in which:
    the energy storage module is provided within a unit, and
    a peripheral device that is distinct from the unit is configured to be carried by the ambulatory patient, is configured to be in electronic communication with the unit, and includes the user trigger module.

9. The WMS of claim 8, in which: the peripheral device is part of the WMS.

10. The WMS of claim 8, in which: the user trigger module includes a touchscreen on the peripheral device.

11. The WMS of claim 8, in which:
    the peripheral device includes the microphone, and
    the user trigger module is a voice recognition module within the peripheral device, and which is designed to:
        receive the audio signal,
        recognize, within the audio signal, a preset voice prompt, and
        generate the trigger input responsive to thus recognizing the preset voice prompt.

12. The WMS of claim 1, wherein the exportable computer file comprises at least electrocardiogram (ECG) signals and the audio data recorded during the predetermined time interval.

13. The WMS of claim 1, wherein the one or more processors are further programmed to cause, responsive to the shock criterion being met, at least some of the stored electrical charge to be discharged via the therapy electrode through the ambulatory patient while the support structure is worn by the ambulatory patient, to deliver a shock to the ambulatory patient.

14. A method for a wearable medical system (WMS), the WMS including at least a support structure configured to be worn by an ambulatory patient, a sensor configured to sense one or more parameters of the ambulatory patient, a measurement circuit configured to render a patient input responsive to the sensed one or more parameters, an energy storage module configured to store an electrical charge, a therapy electrode coupled to the energy storage module and configured to be maintained on a body of the ambulatory patient when the support structure is worn by the ambulatory patient, a microphone configured to output an audio signal responsive to ambient sounds, wherein the microphone is further configured to continuously record and discard audio data corresponding to the audio signal, a memory, a user trigger module configured to enable the ambulatory patient to generate a trigger input, and one or more processors, the method comprising:

receiving the patient input responsive to the sensed one or more parameters;

determining, based on the received patient input, whether a shock criterion is met, wherein the shock criterion is met when the one or more parameters cross a threshold value;

issuing, responsive to the shock criterion met, a prompt for a preset amount of time indicating the ambulatory patient to generate the trigger input within the preset amount of time;

detecting the generated trigger input;

causing, responsive to the detected trigger input, the audio data to be recorded in the memory, wherein causing the audio data to be recorded stops the discarding of the audio data, wherein the audio data is recorded for a predetermined time interval, and wherein the audio recordings made prior to the detected trigger input are retained; and creating an exportable computer file comprising the recorded audio data for clinical review.

15. The method of claim 14, further comprising:

stopping the audio data recording in the memory, responsive to a stop audio recording event occurring, wherein the stop audio recording event occurs after the trigger input is generated.

* * * * *